(12) United States Patent
Kirsch et al.

(10) Patent No.: US 6,863,841 B2
(45) Date of Patent: Mar. 8, 2005

(54) OXADIAZOLE DERIVATIVE AND ITS USE AS CHARGE TRANSPORT AND LIGHT EMITTING MATERIAL

(75) Inventors: Peer Kirsch, Darmstadt (DE); Alexander Hahn, Reusselsheim (DE)

(73) Assignee: Merck Patent GmbH, Darmstadt (DE)

( * ) Notice: Subject to any disclaimer, the term of this patent is extended or adjusted under 35 U.S.C. 154(b) by 69 days.

(21) Appl. No.: 10/318,079

(22) Filed: Dec. 13, 2002

(65) Prior Publication Data
US 2003/0166943 A1 Sep. 4, 2003

(30) Foreign Application Priority Data
Dec. 13, 2001 (EP) .............................. 01129306

(51) Int. Cl.$^7$ .............................. C09K 19/34
(52) U.S. Cl. ...................... 252/299.61; 252/299.62; 252/299.2; 548/143; 428/1.1
(58) Field of Search .............................. 548/100, 124, 548/131, 143; 252/299.01, 299.61, 299.62, 299.7, 299.2; 428/1.1, 125

(56) References Cited

U.S. PATENT DOCUMENTS

| | | | |
|---|---|---|---|
| 4,822,144 A | | 4/1989 | Vriens |
| 4,934,791 A | * | 6/1990 | Shimizu et al. .............. 349/107 |
| 5,198,153 A | | 3/1993 | Angelopoulos et al. |
| 5,457,004 A | * | 10/1995 | Mooberry et al. ........... 430/226 |
| 5,656,401 A | | 8/1997 | Ohta et al. ..................... 430/20 |
| 5,892,244 A | | 4/1999 | Tanaka et al. |
| 5,998,804 A | | 12/1999 | Suh et al. |
| 6,136,251 A | * | 10/2000 | Etzbach et al. ........... 264/297.8 |
| 6,423,799 B1 | * | 7/2002 | Berneth et al. ........... 526/218.1 |
| 6,696,110 B1 | * | 2/2004 | Tuffin et al. ................. 428/1.1 |

FOREIGN PATENT DOCUMENTS

| | | | | |
|---|---|---|---|---|
| DE | 38 12 278 A1 | | 11/1988 | |
| DE | 43 07 243 | * | 3/1992 | ........... C07B/37/04 |
| DE | 195 04 224 A1 | | 8/1995 | |
| EP | 0 261 712 | | 3/1988 | |
| EP | 0 360 618 | | 3/1990 | |
| EP | 0 458 325 A1 | | 11/1991 | |
| EP | 0 528 662 A1 | | 2/1993 | |
| EP | 0 889 350 A1 | | 1/1999 | |
| EP | 0 889 350 | * | 1/1999 | ......... G02F/1/1335 |
| JP | 2000 290284 | | 10/2000 | |
| WO | WO 93/22397 | | 11/1993 | |
| WO | WO 95/22586 | | 8/1995 | |
| WO | WO 96/21659 | | 7/1996 | |
| WO | WO 97/00600 | | 1/1997 | |
| WO | WO 00/57239 | | 9/2000 | |
| WO | WO 00/79617 A1 | | 12/2000 | |

OTHER PUBLICATIONS

English translation of Japanese Abstract 2000–290284.*

* cited by examiner

*Primary Examiner*—Mark F. Huff
*Assistant Examiner*—Jennifer R. Sadula
(74) *Attorney, Agent, or Firm*—Millen, White, Zelano, Branigan, P.C.

(57) ABSTRACT

New oxadiazole derivatives comprising one or more identical or different recurring units of formula I

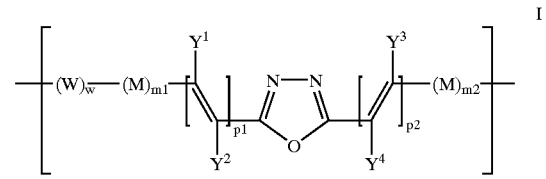

wherein W, M, w, m1, m2, p1, p2, and $Y^1$ to $Y^4$ are as defined herein are suitable for use in liquid crystalline mixtures, polymerizable and polymer materials.

67 Claims, No Drawings

OXADIAZOLE DERIVATIVE AND ITS USE AS CHARGE TRANSPORT AND LIGHT EMITTING MATERIAL

FIELD OF INVENTION

The invention relates to new oxadiazole derivatives. The invention further relates to their use as a component in a liquid-crystalline mixture. The invention also relates to a liquid-crystalline mixture, a polymerizable liquid-crystalline material and a polymer material. In addition, the invention relates to their use as semiconductor, charge transport, photo-conducting, photo-luminescent and/or electro-luminescent material. The invention further relates to a field effect transistor, a security marking or device, charge injection layer, planarising layer, antistatic film or conducting substrate or pattern for electronic applications or flat panel displays and to a liquid-crystal display element comprising at least one oxadiazole derivative, liquid-crystalline mixture, polymerizable liquid crystal material and/or anisotropic polymer film according to the invention.

BACKGROUND AND PRIOR ART

Luminescent polymers showing photoluminescence as well as polymers showing electroluminescence were proposed to be used in light emitting devices and electrooptical display elements.

The organic light emitting devices or diodes (OLEDs) currently being under intense research consist of at least one emission layer. Common OLEDs are realized using multilayer structures, where an emission layer is sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The sandwich structure is built by vacuum deposition or spin coating techniques which may include a polymerization step before applying the next layer (Meerholz et al., Synthetic Metals 111–112 (2000) 31–34). OLEDs which are available in different colors have the potential of being used as the building blocks of different kind of information displays.

Also anisotropic luminescent polymers are known where the polymer and/or lumophor units are oriented. These emissive materials show anisotropic absorption and/or anisotropic emission of polarized light. The degree of absorption and/or emission of linearly polarized light depends on the relative orientation of the wavevector to the main director of the fluorophor molecules. Such an orientation within the luminescent materials can be achieved by different methods:

incorporation of luminescent molecules into an oriented polymer prior or after the orientation step,
tensile orientation of a ductile luminescent polymer (e.g., the techniques described in WO 00/07525),
rubbing of the luminescent polymer,
applying the Langmuir-Blodgett technique,
oriented growth of the luminescent materials onto oriented substrates, like onto known alignment layers,
polymerization of oriented liquid crystals,
photo-induced alignment,
alignment in electric, magnetic or flow fields.

By using their anisotropic optical characteristics, these materials can replace polarizers and/or color filters which reduce the light efficiency in liquid crystal displays (LCDs) by up to 80% and more. Hence, display devices employing such anisotropic luminescent polymers are described to show a high brigthness and contrast, and furthermore a good viewing angle (Weder et al., Science 279 (1998), 835 and EP 889 350 A1). Using pixel elements of at least three different photoluminescent materials multicolor images may be displayed. In major embodiments of such display devices an anisotropic photoluminescent layer substitutes the polarizer of a conventional backlight—polarizer—light valve—polarizer arrangement, where the light valve uses known electrooptical effects of liquid crystal materials, like the TN- or ECB-effect. A high degree of polarized emission is necessary in embodiments where the photoluminescent layer is arranged directly behind the backlight. Whereas a high degree of polarized absorption is mandatory in devices where the photoluminescent layer is placed behind the light valve.

Methods and compounds to achieve charge transport properties and polarized luminescence from oriented materials as well as their application in displays are reviewed by M. Grell and D. D. C. Bradley, Adv. Mater. 1999,11, 895–905.

A proposed type of display uses polarized electroluminescence as background illumination of LCDs. Luessem et al. (Liquid Crystal 21 (1996), 903) report the fabrication of polymer based LEDs showing polarized electroluminescence. The orientation of the molecules within the light emitting layer was accomplished by the self organization of liquid crystal polymers (LCPs) deposited onto a rubbed polyimide film serving as an alignment layer.

In addition, organic materials have recently shown promise as the active layer in organic based thin film transistors and organic field effect transistors [see H. E. Katz, Z. Bao and S. L. Gilat, *Acc. Chem. Res.*, 2001, 34, 5, 359]. Such devices have potential applications in smart cards, security tags and the switching element in flat panel displays. Organic materials are envisaged to have substantial cost advantages over their silicon analogues if they can be deposited from solution, as this enables a fast, large-area fabrication route.

The performance of the device is principally based upon the charge carrier mobility of the semiconducting material and the current on/off ratio, so the ideal semiconductor should have a low conductivity in the off state, combined with a high charge carrier mobility ($>1\times10^{-3}$ cm$^2$ V$^{-1}$ s$^{-1}$). In addition, it is important that the semiconducting material is relatively stable to oxidation, i.e., it has a high ionisation potential, as oxidation leads to reduced device performance.

Compounds, especially dyes, comprising a 2-vinyleneoxadiazole group are known. The documents EP 0 360 618 A2, EP 0 458 325 A1 and DE 38 12 278 C2 are related to photosensitive compositions and describe oxadiazole derivatives as compounds capable of generating acids through irradiation of actinic or radiant rays. The given examples relate to 2-styryl-, 2-(alkylstyryl)-, 2-(alkoxystyryl)-, 2-(4-chlorostyryl)-, 2-(4-styrylstyryl)-, 2-(benzofuran-2-yl)-derivatives of 5-trichloro- and 5-tribromomethyl-oxadiazoles.

The JP 2000/290284-A proposes silane compounds for light-emitting devices. A diphenylsilane containing two 5-phenyl-2-styryl-oxadiazole groups is disclosed among other examples.

The U.S. Pat. No. 5,457,004 provides a high dye-yield coupler for photographic silver halide emulsion layers. The dye group within the coupler may contain a styryl-oxadiazole group.

An aim of this invention is to make available oxadiazole derivatives, which show a mesophase, preferably in a wide temperature range, which are chemically and photochemically stable, and/or stable against an electrochemically induced degradation, and/or which exhibit luminescent and/or charge transport properties.

Another aim of this invention is to make available luminescent oxadiazole derivatives, which themselves or in a liquid-crystalline mixture or in a polymerizable material are especially suitable for the production of anisotropic luminescent materials, especially polymers, showing advantageous anisotropic optical characteristics.

Another aim of the invention is to provide a liquid crystalline mixture, which shows a mesophase in a wide temperature range, which is chemically and photochemically stable, and/or stable against an electrochemically induced degradation, and/or which exhibits luminescent and/or charge transport properties.

Furthermore, it is an aim of the present invention, to provide a polymerizable material, which especially is suited for the production of polymer materials, which exhibit luminescent and/or charge transport properties.

Thus, it is another aim of the present invention, to provide a polymer material, which exhibits luminescent and/or charge transport properties.

Furthermore, it is an aim of the present invention to make available luminescent as well as anisotropic luminescent polymer materials with the above mentioned characteristics.

Further aims of the invention are to extend the pool of mesogenic or liquid crystalline compounds and mixtures, of polymerizable compounds, mixtures or materials, of polymer materials with charge transport and/or luminescent properties and of semiconductor, charge transport, photo-conducting, photo-luminescent and/or electro-luminescent materials available to the expert.

A further aim of this invention is also to show advantageous uses of these oxadiazole derivatives, liquid crystalline mixtures, polymerizable materials and polymer materials.

Further aims of the invention relate to a field effect transistor, a security marking or device and to a liquid-crystal display element.

Another aim of the present invention is to provide a charge injection layer, planarising layer, antistatic film or conducting substrate or pattern for electronic applications or flat panel displays.

Other aims of the present invention are immediately evident to the person skilled in the art from the following detailed description.

Definition of Terms

The term luminescence means emission of electromagnetic radiation, preferably in, but not limited to, the visible spectrum, due to any kind of excitation, preferably by electromagnetic radiation (photoluminescence) or by an applied electric voltage (electroluminescence). The more general term luminescence encompasses phosphorescence and fluorescence, the latter being the preferred meaning.

The term mesogenic group means a rod-shaped, lath-shaped or disk-shaped group, i.e., a group with the ability to induce liquid crystal phase behaviour.

The terms mesogen and mesogenic, liquid crystal and liquid crystalline compound as used in the foregoing and the following comprise compounds with a least one mesogenic group. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerised.

The term 'film' includes self-supporting, i.e., free-standing, films that show more or less pronounced mechanical stability and flexibility, as well as coatings or layers on a supporting substrate or between two substrates.

SUMMARY OF THE INVENTION

One of the objects of the present invention is an oxadiazole derivative comprising one or more identical or different recurring units of formula I

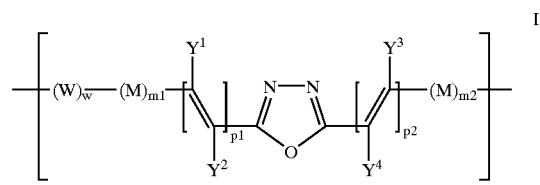

wherein

W is a straight chain or branched alkylene group with 1 to 22 C-atoms, which may be unsubstituted, mono- or poly-substituted by F, Cl, Br, I or CN, it being also possible for one or more $CH_2$ groups to be replaced, in each case independently from one another, by —O—, —S—, —NH—, —NR$^0$—, —CO—, —COO—, —OCO—, —OCO—O—, —S—CO—, —CO—S—, —CH=CH—, —CF=CF— or —C≡C— in such a manner that N, O and/or S atoms are not linked directly to one another, $R^0$ is H or alkyl with 1 to 12 C-atoms, M is, if occuring twice or more, independently of each other, a mesogenic or mesogenity supporting group, $Y^1$ to $Y^4$ are independently of each other H, F, Cl or CN, w is 0 or 1, m1, m2 are independently of each other 0 or 1, whereby m1+m2≧1, and p1, p2 are independently of each other 0 or 1, whereby p1+p2≧1, with the proviso that the group of 5-trichloro- and 5-tribromomethyl-derivatives of the group consisting of 2-styryl-, 2-(alkylstyryl)-, 2-(alkoxystyryl)-, 2-(4-chlorostyryl)-, 2-(4-styrylstyryl)- and 2-(benzofuran-2-yl)-oxadiazoles is not included.

Another object of this invention is a liquid-crystalline mixture having at least two components, at least one of which is liquid-crystalline, characterized in that it comprises at least one oxadiazole derivative according to the invention.

A further object of the invention is a polymerizable material comprising one or more oxadiazole derivatives according to the invention and optionally comprising one or more further compounds, wherein at least one of the oxadiazole derivatives and/or the further compounds is polymerizable.

An additional object of the invention is a polymer material, in particular with charge transport and/or luminescent properties obtainable by polymerising and/or crosslinking a liquid-crystalline mixture and/or a polymerizable material according to the invention.

Furthermore, an object of the invention is an oxadiazole derivative, a liquid-crystalline mixture, a polymerizable material and/or a polymer material according to the invention, which are oxidatively or reductively doped to form conducting ionic species.

A further object of the invention is the use of at least one oxadiazole derivative according to the invention as a component of a liquid-crystalline mixture.

Another object of the invention is the use of at least one oxadiazole derivative, liquid-crystalline mixture, polymerizable material and/or polymer material according to the invention for the manufacture of a semiconductor, charge transport, photo-conducting, photo-luminescent and/or electro-luminescent material.

Further objects of the invention relate to semiconductor, charge transport, photo-conducting, photo-luminescent and/ or electro-luminescent material, characterized in that it comprises at least one oxadiazole derivative, liquid-crystalline mixture, polymerizable material and/or polymer material according to the invention.

A further object of the invention is a field effect transistor, which may be a component of integrated circuitry, a thin film transistor in flat panel display applications, or in a Radio Frequency Identification (RFID) tag, comprising at least one oxadiazole derivative, liquid-crystalline mixture, polymerizable material and/or polymer material according to the invention.

Other objects of the invention relate to a security marking or device comprising at least one oxadiazole derivative, liquid-crystalline mixture, polymerizable material and/or polymer material according to the invention, or a FET or RFID tag according to the invention.

Further objects of the invention relate to charge injection layer, planarising layer, antistatic film or conducting substrate or pattern for electronic applications or flat panel displays, comprising at least one oxadiazole derivative, liquid-crystalline mixture, polymerizable material and/or polymer material according to the invention.

Furthermore, an object of the invention is a liquid-crystal display element, characterized in that it contains at least one oxadiazole derivative, liquid-crystalline mixture, polymerizable material and/or polymer material according to the invention.

Upon further study of the specification and appended claims, further objects and advantages of this invention will become apparent to those skilled in the art.

DETAILED DESCRIPTION OF THE INVENTION

In the following the groups, substituents and indices W, M, $Y^1$, $Y^2$, $Y^3$, $Y^4$, w, m1, m2, p1, p2 have the above given meaning unless stated otherwise.

It is emphasized that each group, substituent and index occuring twice or more in one of the following formulae may have identical or different meanings.

The inventors have found that the oxadiazole derivatives according to the invention exhibit advantageous properties as semiconducting, photoconducting, conducting and/or luminescent materials themselves and/or are especially suitable for the manufacture of materials with such properties. Due to the incorporation of at least one mesogenic or mesogenity supporting group, the oxadiazole derivatives according to the invention are liquid-crystalline and/or support the mesogenity in a liquid-crystalline mixture or a polymer material. Therefore, the oxadiazole derivatives themselves or within a mixture can be oriented by known methods, leading to anisotropic conducting and/or luminescent properties. Especially the low molecular weight derivatives are suited for switchable liquid crystal display elements and exhibit at least one mesophase over a wide temperature range with high clearing temperatures. Whereas the polymerizable oxadiazole derivatives according to the invention have the major advantage that they can be fixed in an oriented state by polymerization and/or crosslinking. Thus, polymer materials with anisotropic conducting and/or luminescent properties are obtainable, which are especially suited as conducting and/or luminescent materials, e.g., in OLEDs. The redox-potential and thus the conducting properties and/or the absorption and/or emission properties can be adjusted by the choice of the substituents, especially by fluorination.

Further advantages of the inventive oxadiazole derivatives are:

they exhibit advantageous absorption and emission characteristics, their emission wavelengths can be tuned, e.g., by the choice of the substituents, in a wide range, especially in the whole visible range, they have a high stability under excitation with UV-light, especially at wavelengths $\lambda \geq 390$ nm, they have a high stability in an electrical field and are electrochemically stable, they show a high ordering tendency in polymerizable mixtures according to the invention yielding a high orientation degree, in an oriented state they show a high degree of optical anisotropy, the starting materials can be obtained commercially or synthesized economically using methods known from the literature and/or as specified in the following, they exhibit a good solubility in polymerizable mixtures, especially in mixtures according to the invention.

The oxadiazole derivative according to the invention is a monomeric, oligomeric or polymeric compound, which exhibits one, two or more of the recurring units of formula I. The polymeric derivatives may be main chain or side chain polymers, in which the recurring units are in the main and/or side chains.

Those oxadiazole derivatives are preferred, in which at least one of the substituents $Y^1$, $Y^2$, $Y^3$, $Y^4$ is F, Cl or CN, most preferably F.

Furthermore, those derivatives are preferred, in which at least both substituents $Y^1$ and $Y^2$ or $Y^3$ and $Y^4$ are F, Cl and/or CN, most preferably F.

The oxadiazole derivative, in which all occuring substituents $Y^1$ to $Y^4$ are F, are very preferred.

The before mentioned derivatives with at least one substituted vinylene-group, especially the fluorinated derivatives, have the advantage of higher clearing temperatures and better stability, e.g., against oxygen, UV-light or electrochemical degradation.

Preferably, both indices m1 and m2 are 1.

Preferably, the mesogenic group M possesses a conjugated π-electron system which is in conjugation with the oxadiazole π-electron system via the vinylene-bridging group. Preferably, M comprises one, two or three aromatic and/or heteroaromatic groups, which may be linked by single bonds or alkylene groups. Thus, the resulting oxadiazole derivatives exhibit advantageous conducting properties and are advantageously used as semiconductor or conductor materials or for the manufacture of such materials, which, in addition, may have electroluminescent properties.

Those oxadiazole derivatives according to the invention are preferred which are liquid-crystalline and thus can be oriented in one of their mesophases to yield materials with advantageous anisotropic electrical and/or optical properties.

Preferred oxadiazole derivatives are those according to formula I1

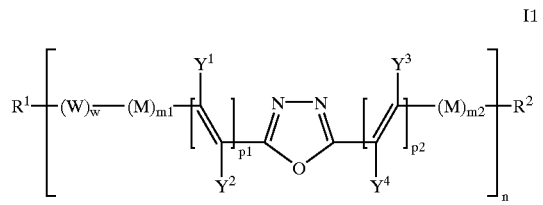

I1 wherein $R^1$, $R^2$ are independently of each other H, halogen, —$NO_2$, —CN, —NCS, straight chain, branched or cyclic alkyl with 1 to 20 C-atoms, which may be unsubstituted, mono- or polysubstituted by F, Cl, Br, I or CN, it being also possible for one or more $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that N, O and/or S atoms are not linked directly to one another, optionally substituted aryl, heteroaryl or arylamino, or P—Sp—X, P is a polymerizable group, Sp is a spacer group or a single bond, and X is —O—, —S—, —$OCH_2$—, —$CH_2O$—, —CO—, —COO—, —OCO—, —OCO—O—, —CO—$NR^0$—, —$NR^0$—CO—, —$OCH_2$—, —$CH_2O$—, —$SCH_2$—, —$CH_2S$—, —CH=CH—COO—, —OOC—CH=CH— or a single bond, $R^0$, $R^{00}$ are independently of each other H or alkyl with 1 to 12 C-atoms, n is 1, 2 or greater than 2.

If n=1, w=0, m1=0 and p1=0, then $R^1$ is not $CCl_3$ or $CBr_3$, preferably. If n=1, m2=0 and p2=0, then $R^2$ is not $CCl_3$ or $CBr_3$, preferably.

n is preferably an integer from 1 to 5000, especially from 1 to 1000, most preferably 1, 2, 3 or 2 to 1000.

If n=1, then w is preferably 0.

If n=2 or greater than 2, then, preferably, w of the first recurring unit (counting from the left) is 0 and w of the second recurring unit and, if applicable, of the following recurring units is 1, such that W is a bridging group between adjacent recurring units.

The polymeric oxadiazole derivatives according to the invention include homopolymers and copolymers, like for example statistically random copolymers, alternating copolymers and block copolymers.

M is preferably a mesogenic or mesogenity supporting group of formula I2

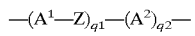

I2 wherein $A^1$, $A^2$ are independently of each other an arylene or heteroarylene group, or a saturated or partially saturated alicyclic or heterocyclic group, having up to 25 C-atoms and being unsubstituted, mono- or polysubstituted with L, L is, if occuring twice or more, independently of each other, F, Cl, CN or alkyl or alkoxy with 1 to 6 C-atoms, which may be mono- or polysubstituted by F, Z is —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^0$—, —CL=CL—, —C≡C—, —CH=CH—COO—, —OCO—CH=CH— or a single bond, $R^0$ is H or alkyl with 1 to 12 C-atoms, q1, q2 are independently of each other 0, 1 or 2, whereby q1+q2≧1.

Preferably, $A^2$ is an arylene or heteroarylene group, forming a conjugated π-electron system with the vinylene-oxadiazole unit.

Arylene and heteroarylene preferably denote a bivalent mono-, bi- or tricyclic aromatic or heteroaromatic radical with up to 25 C-atoms wherein the rings can be fused and the heteroaromatic groups contain at least one hetero ring atom, preferably selected from N, O, and S. The arylene and heteroarylene groups are optionally substituted by one or more L groups.

Especially preferred arylene and heteroarylene groups are 1,4-phenylene in which, in addition, one or more CH groups may be replaced by N, naphthalene-2,6-diyl, thiophene-2,5-diyl, thienothiophene-2,5-diyl, dithienothiophene-2,6-diyl, thiophene-1,1-dioxide-2,5-diyl, alkyl fluorene and oxazole, all of which can be unsubstituted, mono- or polysubstituted with L as defined above.

The saturated or partially saturated alicyclic or heterocyclic groups for $A^1$ or $A^2$ preferably denote a bivalent, mono-, bi- or tricyclic, saturated or partially saturated, alicyclic or heteroalicyclic group with up to 25 C atoms wherein rings may be fused and the heteroalicyclic groups contain at least one hetero ring atom, preferably selected from N, O, and S. These alicyclic or heteroalicyclic groups are optionally substituted with one or more L groups.

Preferably, $A^1$, $A^2$ are independently of one another a) trans-1,4-cyclohexylene, in which, in addition, one or more non-adjacent $CH_2$ groups may in each case independently be replaced by —O— and/or —S—, b) a radical from the group consisting of 1,4-cyclohexenylene, 1,4-bicyclo[2.2.2]octylene, piperidine-1,4-diyl, decahydronaphthalene-2,6-diyl and 1,2,3,4-tetrahydronaphthalene-2,6-diyl, or c) 1,4-phenylene, in which, in addition, one or two CH groups may in each case be replaced by N, d) a radical from the group consisting of naphthalene-2,6-diyl, phenanthrene-diyl and anthracene-2,6-, -2,7- and -9,10-diyl, whereby in each case, one or two CH groups may in each case be replaced by N, e) a radical from the group consisting of furane, thiophene, thiophene-S,S-dioxide, oxazole, oxadiazole, pyrrole, imidazole, thiazole, thiadiazole-2,4- and -2,5-diyl, in which the radicals of the groups a), b), c), d) and e) may also be mono- or polysubstituted by L, as defined above.

Preferably, $A^2$ is a radical of the groups c), d) or e), especially c). Preferably, $A^1$ is a radical of the groups a) to e), especially a) or c).

According to a first embodiment of the invention, preferred oxadiazole derivatives are characterized by formula II

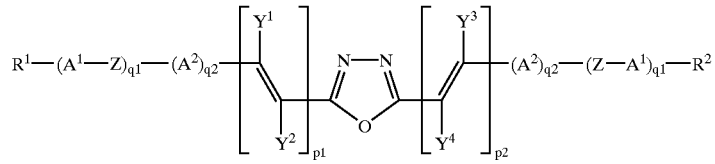

II wherein $Y^1$ to $Y^4$, p1, p2, $R^1$, $R^2$, $A^1$, $A^2$, Z, q1 and q2 are, if occuring twice or more, independently of each other, as defined above.

Those oxadiazole derivatives of the formula II are preferred, wherein:

if p1=1, then at least one of the substituents $Y^1$, $Y^2$ is F, Cl or CN, and/or
if p2=1, then at least one of the substituents $Y^3$, $Y^4$ is F, Cl or CN.
if p1=1, then both substituents $Y^1$, $Y^2$ are independently of each other F, Cl or CN, and/or
if p2=1, then both substituents $Y^3$, $Y^4$ are independently of each other F, Cl or CN.
if p1=1, then both substituents $Y^1$, $Y^2$ are F, and/or
if p2=1, then both substituents $Y^3$, $Y^4$ are F.
at least one of the two indices q2 is 1.
the sum over all indices q1 and q2 is 1, 2, 3 or 4.
$R^1$ and/or $R^2$ are $C_1$–$C_{12}$-alkyl, $C_2$–$C_{12}$-alkenyl and/or $C_1$–$C_{12}$-alkoxy, which are optionally substituted with one or more fluorine atoms.
$R^1$ and/or $R^2$ are a polymerizable group P—Sp—X—.

Preferred oxadiazole derivatives, according to the first embodiment, with one or two fluorinated vinylene groups are of the formula IIa

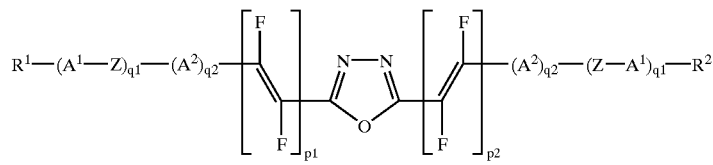

IIa wherein p1, p2, $R^1$, $R^2$, $A^1$, $A^2$, Z, q1, q2 are, if occuring twice or more, independently of each other, identical or different, as defined above.

Preferred oxadiazole derivatives according to formula II are those according to formulae II.1 to II.22, wherein $R^1$, $R^2$, $Y^1$, $Y^2$, $Y^3$, $Y^4$ are as defined above and below, and wherein each 1,4-phenylene group and/or each thiophenylene groups may be substituted by 1 to s substituents L, in particular by F, with s=4 for phenylene and s=2 for thiophenylene.

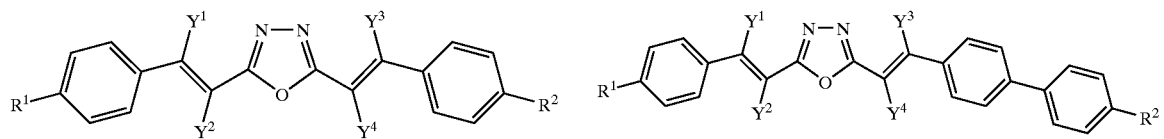
II.1
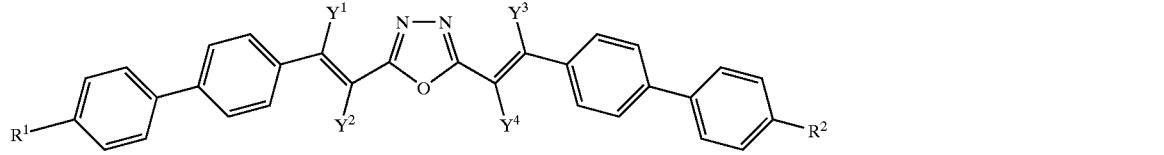
II.2
II.3
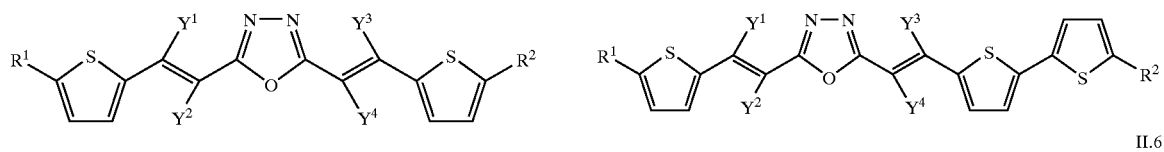
II.4
II.5
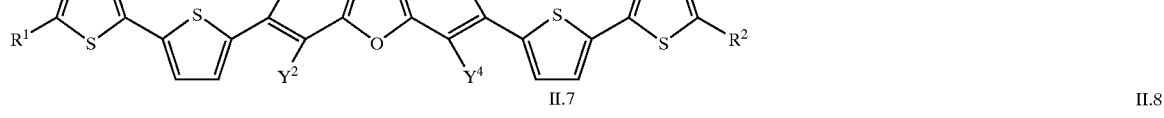
II.6
II.7
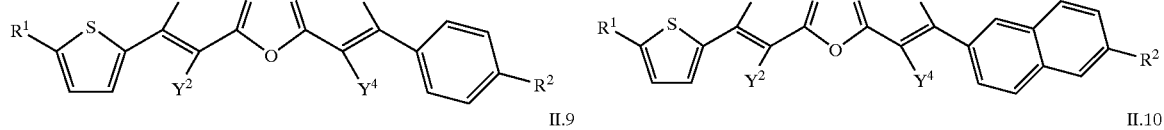
II.8
II.9
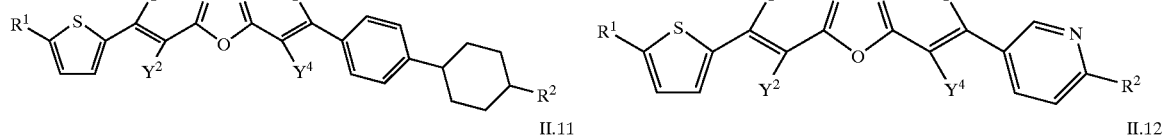
II.10
II.11
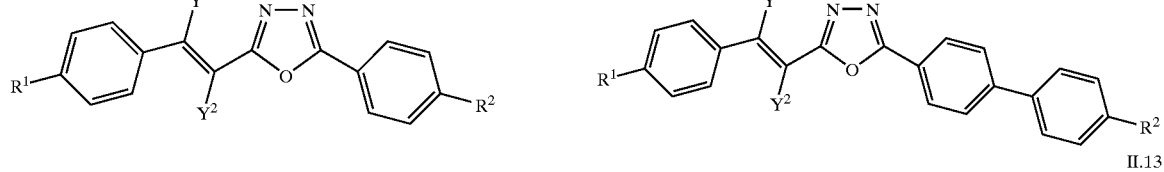
II.12
II.13
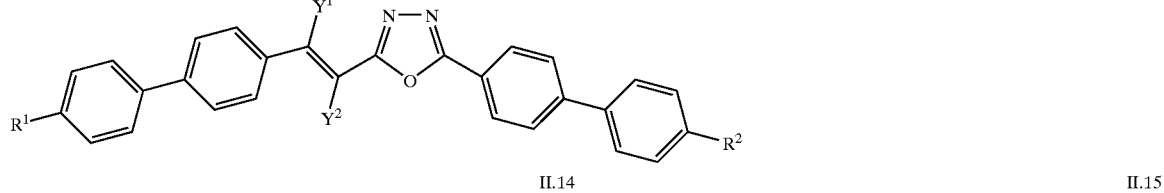
II.14
II.15
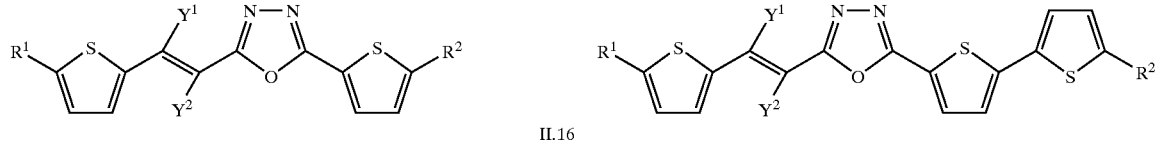
II.16
II.17
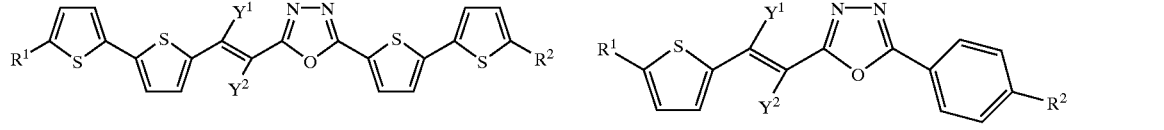

II.18
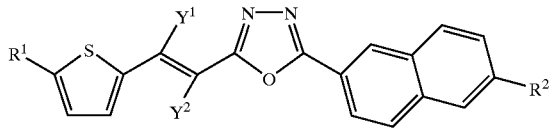

II.19
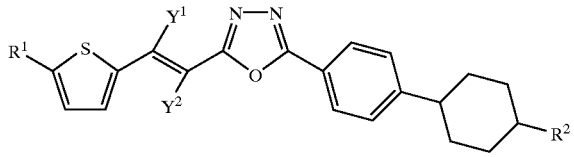

II.20
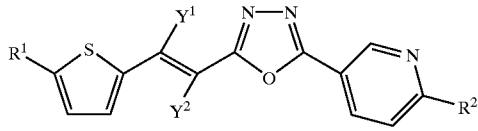

II.21
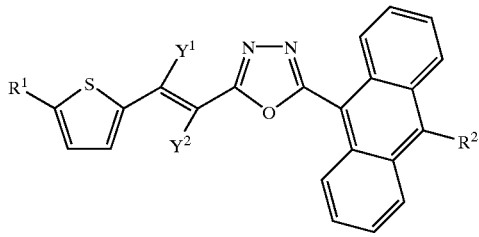

II.22
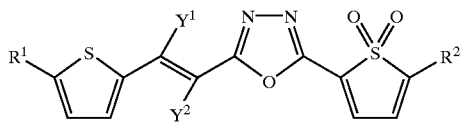

According to a second embodiment of the invention, preferred oxadiazole derivatives are characterized by formula III III
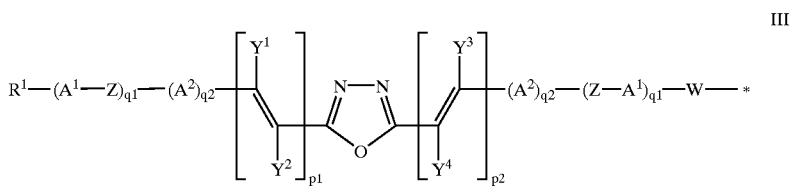

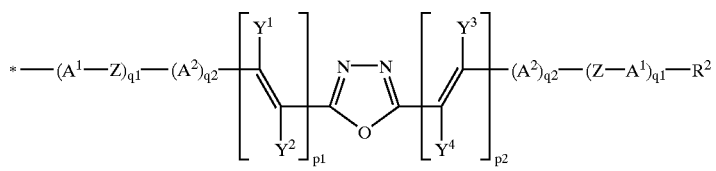

wherein W, $Y^1$ to $Y^4$, p1, p2, $R^1$, $R^2$, $A^1$, $A^2$, Z, q1 and q2 are, if occuring twice or more, independently of each other, as defined above.

Those oxadiazole derivatives of the formula III are preferred, wherein:

- if an index p1 is 1, then at least one of the corresponding substituents $Y^1$, $Y^2$ is F, Cl or CN, and/or
  if an index p2 is 1, then at least one of the corresponding substituents $Y^3$, $Y^4$ is F, Cl or CN.
- if an index p1 is 1, then both corresponding substituents $Y^1$, $Y^2$ are independently of each other F, Cl or CN, and/or
  if an index p2 is 1, then both corresponding substituents $Y^3$, $Y^4$ are independently of each other F, Cl or CN.
- if an index p1 is 1, then both corresponding substituents $Y^1$, $Y^2$ are F, and/or
  if an index p2 is 1, then both corresponding substituents $Y^3$, $Y^4$ are F.
- at least one index q2 is 1.
- the sum over all indices q1 and q2 is 2, 3, 4, 5, 6, 7 or 8.
- W is a group of formula I3, as defined in the following.
- $R^1$ and/or $R^2$ are $C_1$–$C_{12}$-alkyl, $C_2$–$C_{12}$-alkenyl and/or $C_1$–$C_{12}$-alkoxy, which are optionally substituted with one or more fluorine atoms.
- $R^1$ and/or $R^2$ are a polymerizable group P—Sp—X—.

Preferred oxadiazole derivatives, according to the second embodiment, with one or more fluorinated vinylene groups are of the formula IIIa

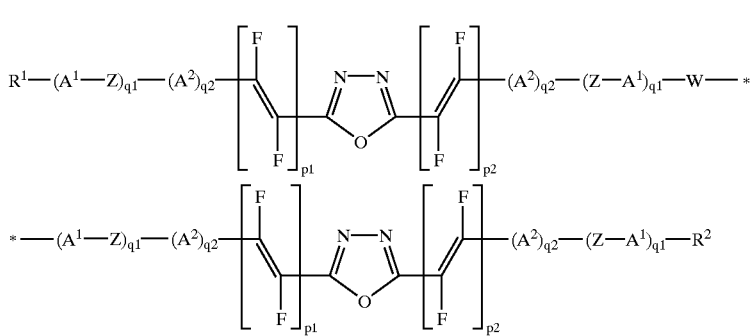

IIIa wherein W, p1, p2, $R^1$, $R^2$, $A^1$, $A^2$, Z, q1, q2 are, if occuring twice or more, independently of each other, identical or different, as defined above.

Preferred oxadiazole derivatives according to formula III are those according to formulae III.1 to III.6, wherein $R^1$, $R^2$, $Y^1$, $Y^2$, $Y^3$, $Y^4$ are as defined above and below, and wherein each 1,4-phenylene group and/or each thiophenylene groups may be substituted by 1 to s substituents L, in particular by F, with s=4 for phenylene and s=2 for thiophenylene.

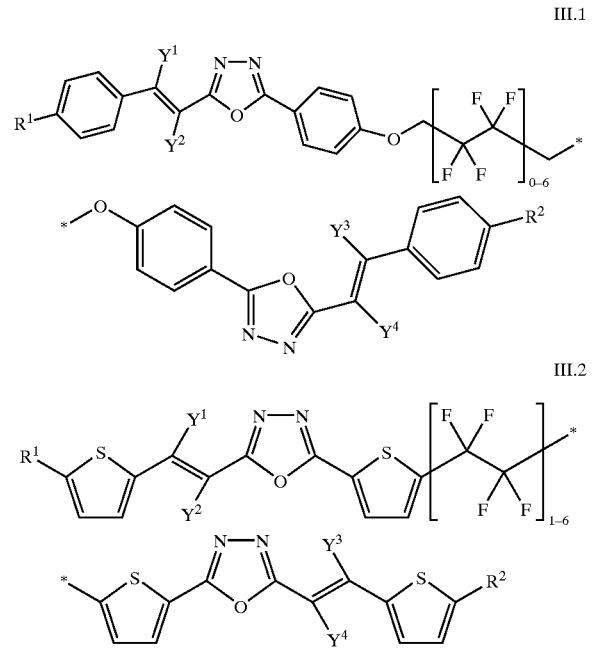

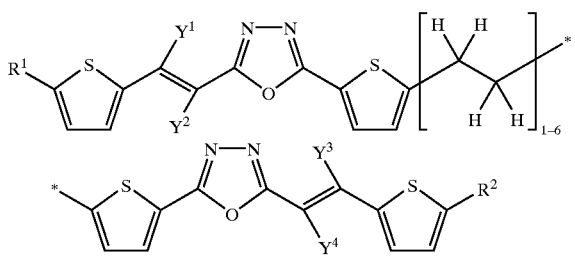

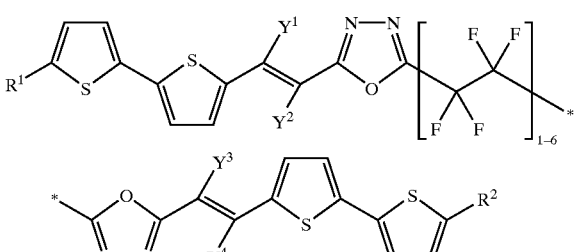

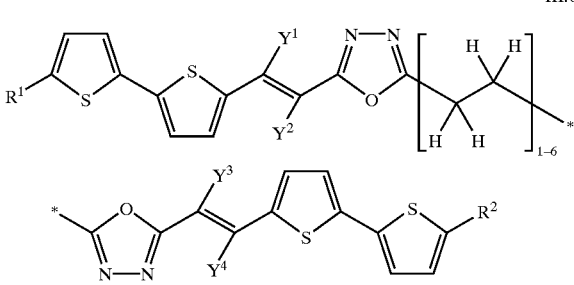

In the inventive oxadiazole derivatives, W is preferably a bridging group of formula I3

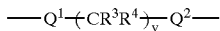

wherein
$Q^1$, $Q^2$ are independently of each other —O—, —S—, —COO—, —OCO—, —CO— or a single bond,
$R^3$, $R^4$ are independently of each other H, F, Cl, CN or alkyl or alkoxy with 1 to 6 C-atoms, both of which may be mono- or polysubstituted by F, and
v is 1 to 20.

Those bridging groups of the formula I3 are preferred, wherein $v \geq 2$, most preferably $v \geq 4$.

$R^3$, $R^4$ are independently of each other H or F.

$v \geq 4$ and at least four substituents $R^3$, $R^4$ are F, the other substituents $R^3$, $R^4$ are H.

$Q^1$, $Q^2$ are —O— or a single bond.

Preferred oxadiazole derivatives are those, in which at least one of the substituents $Y^1$, $Y^2$ for which p1=1, and/or at least one of the substituents $Y^3$, $Y^4$, for which p2=1, are independently of each other F, Cl and/or CN.

Those oxadiazole derivatives are most preferred, wherein the substituents $Y^1$, $Y^2$, for which p1=1, and/or the substituents $Y^3$, $Y^4$, for which p2=1, are F.

A preferred embodiment of the present invention relates to derivatives of formula I1 that are mesogenic or liquid crystalline, and very preferably comprise one or more polymerizable groups. Very preferred materials of this type are monomers and oligomers of formula I wherein n is an integer from 1 to 15 and $R^1$ and/or $R^2$ denote P—Sp—X.

Another preferred embodiment encompasses all those oxadiazole derivatives which are polymerizable, especially in which one or both of radicals $R^1$ and $R^2$ denote P—Sp—X. Particularly preferred oxadiazole derivatives with one or two P—Sp—X are the compounds of the formula II, especially of the formulae IIa and II.1 to II.22, and the compounds of the formula III, especially of the formulae IIIa and III.1 to III.6.

The polymerizable group P is preferably selected from $CH_2=CW^1$—COO—,

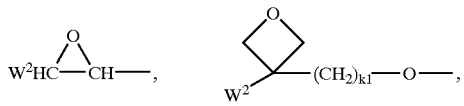

$CH_2=CW^2$—O—, $CH_3$—CH=CH—O—, HO—$CW^2W^3$—, HS—$CW^2W^3$—, $HW^2N$—, HO—$CW^2W^3$—NH—, $CH_2=CW^1$—CO—NH—, $CH_2$=CH—(COO)$_{k1}$-Phe-(O)$_{k2}$—, Phe-CH=CH—, HOOC—, OCN— and $W^4W^5W^6$Si—, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and k1 and k2 being independently of each other 0 or 1.

Especially preferred polymerizable groups P are $CH_2$=CH—COO—, $CH_2=C(CH_3)$—COO— and

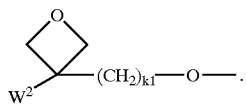

Very preferred are acrylate and oxetane groups. Oxetanes produce less shrinkage upon polymerisation (cross-linking), which results in less stress development within films, leading to higher retention of ordering and fewer defects. Oxetane cross-linking is advantageously performed with a cationic initiator, which unlike free radical initiator is inert to oxygen.

As for the spacer group Sp all groups can be used that are known for this purpose to those skilled in the art. The spacer group Sp is preferably a linear or branched alkylene group having 1 to 20 C-atoms, in particular 1 to 12 C-atoms, in which, in addition, one or more non-adjacent $CH_2$ groups may in each case be replaced by —O—, —S—, —NH—, —N($CH_3$)—, —CO—, —O—CO—, —S—CO—, —O—COO—, —CO—S—, —CO—O—, —CH(halogen)-, —C(halogen)$_2$, —CH(CN)—, —CH≡CH—, —C≡C— or a siloxane group.

Typical spacer groups are for example —($CH_2$)$_p$—, —($CH_2CH_2$O)$_r$—$CH_2CH_2$—, —$CH_2CH_2$—S—$CH_2CH_2$— or —$CH_2CH_2$—NH—$CH_2CH_2$— or —(SiR$^\circ$R$^{\circ\circ}$—O)$_p$—, with p being an integer from 2 to 12, r being an integer from 1 to 3 and R$^\circ$ and R$^{\circ\circ}$ having the previously defined meanings.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyl-iminoethylene, 1-methylalkylene, ethenylene, propenylene and butenylene for example.

Further preferred are compounds with one or two groups P—Sp—X wherein Sp and/or X is a single bond.

In case of compounds with two groups P—Sp—X, each of the two polymerizable groups P, the two spacer groups Sp, and the two linkage groups X can be identical or different.

Preferably, $R^1$ and/or $R^2$ are selected from $C_1$–$C_{20}$-alkyl, $C_2$–$C_{20}$-alkenyl, $C_2$–$C_{20}$-alkynyl, $C_1$–$C_{20}$-alkoxy, $C_1$–$C_{20}$-oxaalkyl, $C_1$–$C_{20}$-thioether, $C_1$–$C_{20}$-silyl, $C_1$–$C_{20}$-ester, $C_1$–$C_{20}$-amino, in particular $C_1$–$C_{12}$-alkyl, $C_2$–$C_{12}$-alkenyl, $C_1$–$C_{12}$-alkoxy, which in each case are optionally substituted with one or more fluorine atoms. Preferably, $R^1$ and $R^2$ are not $CCl_3$ or $CBr_3$.

In addition, $R^1$ and/or $R^2$ are preferably push-pull groups, i.e., groups with electron pair acceptor and/or donor properties, like, e.g., —$NO_2$, —CN, —NCS, alkoxy, alkylthio, dialkylamino, alkylarylamino and diarylamino. Very preferably, the push-pull group or groups are directly linked with the vinylene-oxadiazole group or linked with it via a conjugated π-electron system. By the choice of the push-pull groups or group, the electronic properties of the oxadiazole derivative according to the invention and thus their optical properties, in particular their absorption and emission wavelengths, can be determined. Therefore, by the choice of $R^1$ and/or $R^2$ and, in addition, of substituents of aryl and/or heteroaryl groups, the luminescent color of the oxadiazole derivative according to the invention and of a material comprising such oxadiazole derivatives can be tuned over the whole visible spectrum of wavelengths.

Aryl and heteroaryl preferably denote a mono-, bi- or tricyclic aromatic or heteroaromatic group with up to 25 C atoms, wherein rings can be fused and heteroaromatic groups contain at least one hetero ring atom, preferably selected from N, O, and S. The aryl and heteroaryl groups are optionally substituted with one or more of halogen, —$NO_2$, —CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —NR$^\circ$, —SiR$^\circ$R$^{\circ\circ}$—, —CO—, —COO—, —OCO—, —OCO—O—, —S—CO—, —CO—S—, —CH=CH— or —C≡C— in such a manner that N,O and/or S atoms are not linked directly to one another.

The term phenylene, which may be substituted by 1 to 4 substituents L, has one of the following meanings

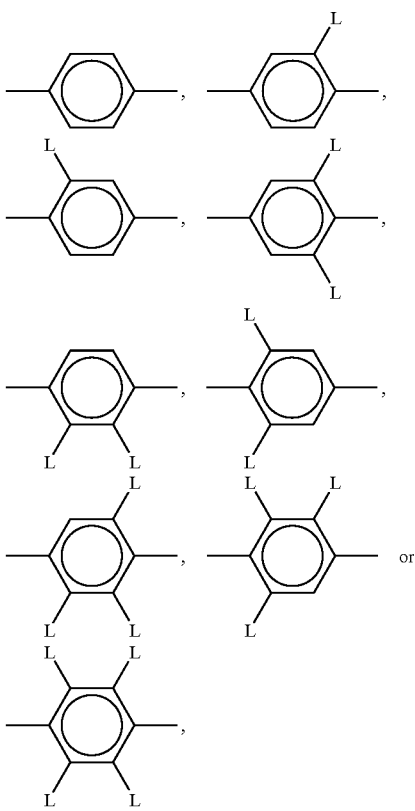

wherein L is as defined above, in particular F.

The term thiophenylene, which may be substituted by 1 to 2 substituents L, has one of the following meanings

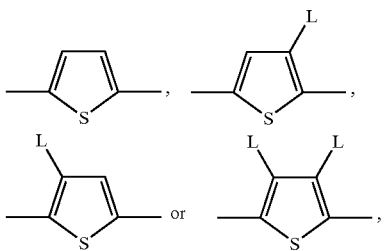

wherein L is as defined above, in particular F or alkyl, being unsubstituted, mono-, poly- or perfluorinated.

If in the formulae shown above and below a substituent, in particular $R^1$, $R^2$, is an alkyl or alkoxy radical, i.e. where the terminal $CH_2$ group is replaced by —O—, this may be straight-chain or branched. It is preferably straight-chain, has 2 to 8 carbon atoms and accordingly is preferably ethyl, propyl, butyl, pentyl, hexyl, heptyl, octyl, ethoxy, propoxy, butoxy, pentoxy, hexyloxy, heptoxy, or octoxy, furthermore methyl, nonyl, decyl, undecyl, dodecyl, tridecyl, tetradecyl, pentadecyl, methoxy, nonoxy, decoxy, undecoxy, dodecoxy, tridecoxy or tetradecoxy, for example.

Oxaalkyl, i.e., where one $CH_2$ group is replaced by —O—, is preferably straight-chain 2-oxapropyl(= methoxymethyl), 2-(=ethoxymethyl) or 3-oxabutyl(=2-methoxyethyl), 2-, 3-, or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Fluorinated alkyl is preferably $C_iF_{2i+1}$, wherein i is an integer from 1 to 12, in particular $CF_3$, $C_2F_5$, $C_3F_7$, $C_4F_9$, $C_5F_{11}$, $C_6F_{13}$, $C_7F_{15}$ or $C_8F_{17}$.

Halogen is preferably F or Cl.

The oxadiazole derivatives of the present invention can be synthesized according to or in analogy to known methods. Some preferred methods are described below. Although the following synthesis schemes refer to fluorine substituted vinylene bridged compounds, those derivates with chlorine and/or —CN substituted vinylene bridges are obtained by applying these methods in an analogous manner. Further methods of preparation can be taken from the examples.

The synthesis of symmetrically substituted oxadiazoles is illustrated by the synthesis scheme 1.

Scheme 1:

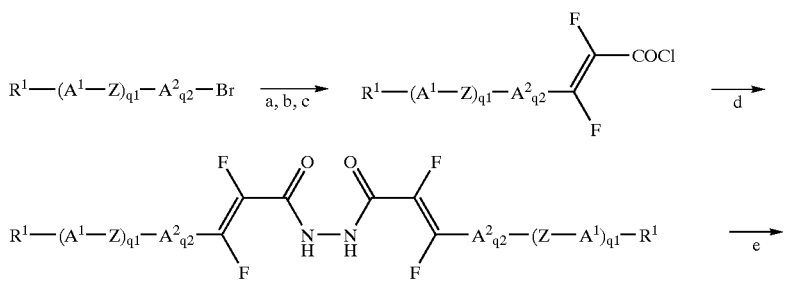

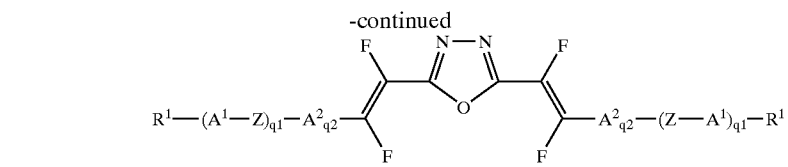

a) 1. Mg, THF; 2. $CF_2$=CFCl, from -40° C. to 20° C..
b) 1. BuLi, n-pentane, $Et_2O$, -100° C.. 2. $CO_2$.
c) $SOCl_2$.
d) $N_2H_4 \cdot H_2O$, THF.
e) $POCL_3$.

The synthesis of unsymmetrically substituted oxadiazoles is given by the following scheme 2.

Scheme 2:

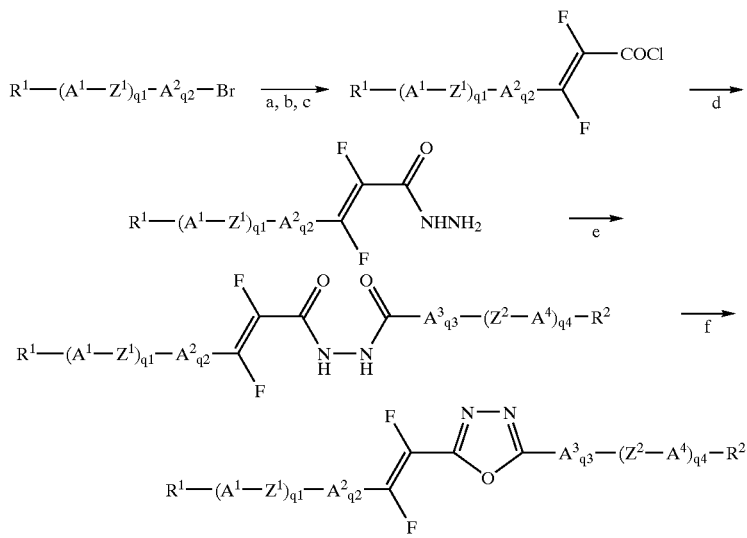

a) 1. Mg, THF; 2. $CF_2$=CFCl, from -40° C. to 20° C..
b) 1. BuLi, n-pentane, $Et_2O$, -100° C.; 2. $CO_2$.
c) $SOCl_2$.
d) $N_2H_4 \cdot H_2O$, THF.
e) $R^2$—$(A^4$—$Z^2)_{q4}$—$A^3_{q3}$—COCl, $NEt_3$, THF.
f) $POCl_3$.

The preparation of oxadiazole dimeres is illustrated by the synthesis schemes 3 and 4.

Scheme 3:

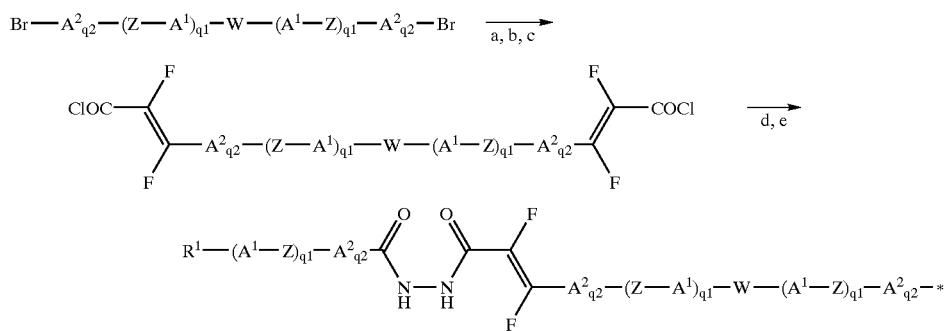

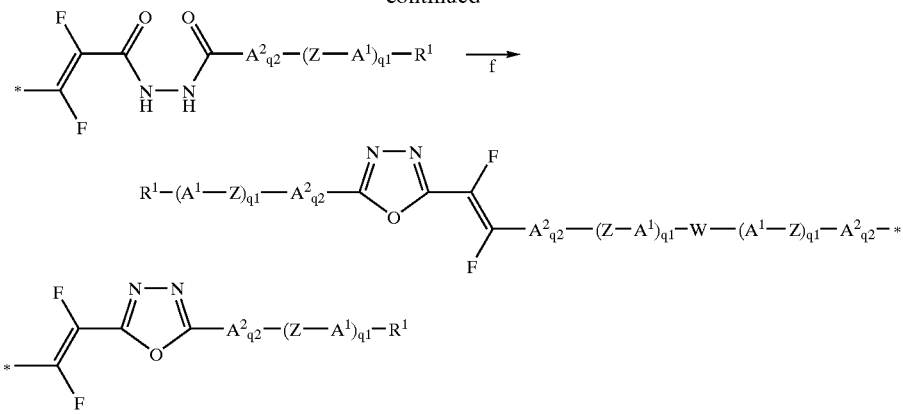

a) 1. Mg, THF; 2. CF$_2$=CFCl, from -40° C. to 20° C..
b) 1. BuLi, n-pentane, Et$_2$O, -100° C.; 2. CO$_2$.
c) SOCl$_2$.
d) N$_2$H$_4$·H$_2$O, THF.
e) R$^1$—(A$^1$—Z)$_{q1}$—A$^2_{q2}$—COCl, NEt$_3$, THF.
f) POCl$_3$.

Scheme 4:

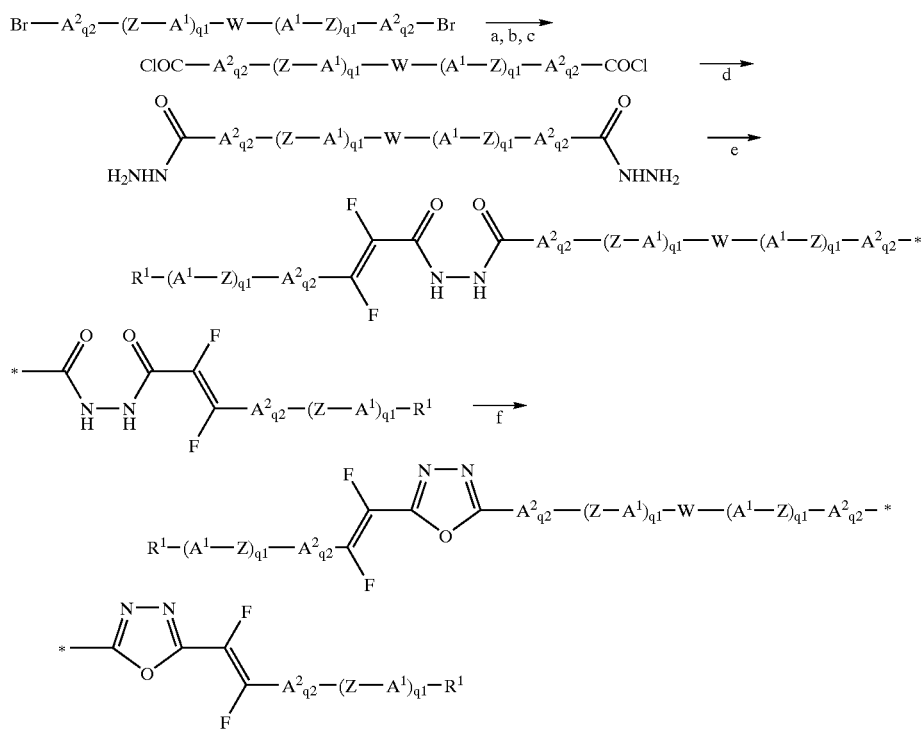

a) Mg, THF;
b) CO$_2$.
c) SOCl$_2$.
d) N$_2$H$_4$·H$_2$O, THF.
e) R$^1$—(A$^1$—Z)$_{q1}$—A$^2_{q2}$—CF=CFCOCl, NEt$_3$, THF.
f) POCl$_3$.

The polymerizable compounds as disclosed in the foregoing and the following can be prepared by methods which are known per se and which are described in the documents cited above and, for example, in standard works of organic chemistry such as, for example, Houben-Weyl, Methoden der organischen Chemie, Thieme-Verlag, Stuttgart.

The liquid-crystalline mixture according to this invention has at least two components, at least one of which is liquid-crystalline, and it comprises at least one oxadiazole derivative according to this invention.

Components of the liquid-crystalline mixture, other than the inventive oxadiazole derivatives, can be chosen from the pool of the liquid-crystalline compounds and co-components of liquid-crystalline mixtures, like, e.g., stabilizers or chiral dopants, which are known to the person skilled in the art. The components and their concentrations can be chosen according to known liquid-crystalline mixtures, especially of those for electro-optical display applications, like, e.g., TN-, TFT- or STN-applications. Preferred components are for example oligo-thiophene derivatives, terphenyl derivatives, quaterphenyl derivatives and oxadiazole derivatives.

Thus, the oxadiazole derivatives according to the invention can be used as components of liquid-crystalline media, in particular for displays based on the principle of the twisted cell, the guest-host effect, the effect of deformation of aligned phases DAP or ECB (electrically controlled birefringence), the IPS (in-plane switching) effect or the effect of dynamic scattering. Another preferred application is the use of the inventive derivatives in a device based on the principle of polarizing excitonic energy transfer (EET), e.g. described by M. Grell and D. D. C. Bradley, Adv. Mater. 1999, 11, 895–905 and the literature cited therein. According to this application, luminescent oxadiazole molecules are "guest" molecules being oriented by a switchable LC host, comprising at least one sensitizer as a co-component. The incoming light is absorbed by the sensitizer, which passes its excitation to the oriented luminescent oxadiazole molecules, leading to a polarized emission of light, being switchable in its direction by the LC host.

Preferably, at least one component of the liquid-crystalline mixture is polymerizable and/or crosslinkable. Thus, the molecules of the components can be oriented by known methods and this orientation can be frozen by a following polymerization and/or crosslinking process, yielding a material, with anisotropic properties.

The at least one component, which is polymerizable and/or crosslinkable, can be a co-component of the mixture, i.e., not being an oxadiazole derivative according to this invention. In this case, the oxadiazole derivative is embedded as "guest" molecules in the polymer matrix formed by a "host" matrix of the co-components, which might be unidirectionally oriented or not.

Preferably, the liquid-crystalline mixture comprises at least one oxadiazole derivative, that is polymerizable and/or crosslinkable. In this embodiment, the oxadiazole component itself, which is advantageously liquid-crystalline, can be frozen in its oriented or unoriented state permanently.

Particularly preferred are polymerizable liquid-crystal mixtures having a nematic and/or smectic phase. For FET applications smectic materials are especially preferred. For OLED applications nematic or smectic materials are especially preferred.

The polymerizable material according to the invention comprises one or more inventive oxadiazole derivatives and optionally one or more further compounds, wherein at least one of the oxadiazole derivatives and/or the further compounds is polymerizable.

Preferably, at least one of the oxadiazole derivatives is mesogenic or liquid-crystalline and polymerizable or crosslinkable.

Preferably, the polymerizable material comprises one or more further compounds, wherein at least one of the further compounds is polymerizable.

Another object of this invention is a polymer material, in particular with charge transport and/or luminescent properties, obtainable by polymerising and/or crosslinking a liquid-crystalline mixture and/or a polymerizable material according to this invention.

Preferably, the polymer material exhibits anisotropic charge transport and/or optical, in particular luminescent properties.

A preferred polymer material is obtainable by a process comprising the following steps
a) forming a thin layer of the polymerizable liquid-crystalline mixture and/or the polymerizable material according to the invention,
b) aligning molecules of the compounds of the mixture in the thin layer into a uniform orientation or a patterned orientation such that in each pattern the orientation is uniform,
c) polymerizing said liquid-crystalline mixture and/or the polymerizable material.

Preferably the step a) is performed by coating a thin layer of the polymerizable mixture or material onto a carrier material or onto a substrate or between two substrates. The thin film has preferably a thickness in the range of 1 $\mu$m to 5 mm, especially 1 $\mu$m to 1 mm, most preferably in the range of 2 $\mu$m to 500 $\mu$m. If one or two substrates are used, after the polymerizing step c) one or both substrates are removed preferably. Advantageously the carrier material and/or the substrate are transparent, at least in the wavelength range of the excitation and/or emission of the luminescent polymer material. By this procedure a luminescent polymer film of the above thickness is obtained, which may be structured or unstructured. The structuring may be achieved by applying the luminescent polymer material on a patterned substrate or the material or the film is patterned by known techniques like lithography.

Polymerisation is preferably carried out by in-situ polymerisation of a coated layer of the mixture or material according to this invention, preferably during fabrication of the electronic or optical device. In case of liquid-crystal materials, these are preferably aligned in their liquid-crystal state into homeotropic orientation prior to polymerisation, where the conjugated $\pi$-electron systems are orthogonal to the direction of charge transport. This ensures that the intermolecular distances are minimized and hence then energy required to transport charge between molecules is minimised. The molecules are then polymerised or crosslinked to fix the uniform orientation of the liquid-crystal state. Alignment and curing are carried out in the liquid-crystal phase or mesophase of the material. This technique is known in the art and is generally described for example in D. J. Broer, et al., Angew. Makromol. Chem. 183, (1990), 45–66.

Alignment of the liquid crystal material can be achieved by methods described in the introduction, like, e.g., by treatment of the substrate onto which the material is coated, by shearing the material during or after coating, by application of a magnetic or electric field to the coated material, or by the addition of surface-active compounds to the liquid-crystal material. Reviews of alignment techniques are given for example by I. Sage in "Thermotropic Liquid Crystals", edited by G. W. Gray, John Wiley & Sons, 1987, pages 75–77, and by T. Uchida and H. Seki in "Liquid Crystals—Applications and Uses Vol. 3", edited by B. Bahadur, World Scientific Publishing, Singapore 1992, pages 1–63. A review of alignment materials and techniques is given by J. Cognard, Mol. Cryst. Liq. Cryst. 78, Supplement 1 (1981), pages 1–77.

Polymerisation takes place by exposure to heat or actinic radiation. Actinic radiation means irradiation with light, like UV light, IR light or visible light, irradiation with X-rays or gamma rays or irradiation with high energy particles, such as ions or electrons. Preferably polymerisation is carried out by UV irradiation at a non-absorbing wavelength. As a source for actinic radiation for example a single UV lamp or a set of UV lamps can be used. When using a high lamp power the curing time can be reduced. Another possible source for actinic radiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. When curing polymerizable materials with acrylate or methacrylate groups, preferably a radical photoinitiator is used, when curing polymerizable materials with vinyl, epoxide and oxetane groups, preferably a cationic photoinitiator is used. It is also possible to use a polymerisation initiator that decomposes when heated to produce free radicals or ions that start the polymerisation. As a photoinitiator for radical polymerisation for example the commercially available Irgacure 651, Irgacure 184, Darocure 1173 or Darocure 4205 (all from Ciba Geigy AG) can be used, whereas in case of cationic photopolymerisation the commercially available UVI 6974 (Union Carbide) can be used.

The polymerizable material can additionally comprise one or more other suitable components such as, for example, catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Oxadiazole derivatives comprising one or more groups P—Sp—X can also be copolymerised with polymerizable mesogenic compounds to induce, or, enhance liquid-crystal phase behaviour. Polymerizable mesogenic compounds that are suitable as comonomers are known in the prior art and disclosed, for example, in WO 93/22397 A1, EP 0 261 712 A1, DE 195 04 224 A1, WO 95/22586 A1 and WO 97/00600 A2, which are incorporated herein by reference.

To exclude oxygen that may inhibit the free radical polymerization, a layer, e.g., comprising PET, may be laminated on top of the thin layer, or alternatively the curing can be carried out under a nitrogen atmosphere. When using a cationic photoinitiator oxygen exclusion is not needed, but water should be excluded.

Since the mixture or material may contain both polymerizable components with one (monofunctional) and with two or more polymerizable groups (multifunctional), polymerization and crosslinking are carried out in the same process.

By varying the concentration of the multifunctional mesogenic or non mesogenic components the crosslink density and thereby the product properties, such as the glass transition temperature, the temperature dependence of the optical properties, the thermal and mechanical stability and the solvent resistance can be tuned easily.

These methods, however are only to be understood as examples that should not limit the scope of the invention. The person skilled in the art can easily find other suitable ways to carry out the polymerization.

A further aspect of the invention relates to both the oxidised and reduced form of the oxadiazole derivatives, the liquid-crystalline mixture, the polymerizable material and the polymer material according to this invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662 A1, U.S. Pat. No. 5,198,153 or WO 96/21659 A1.

The doping process typically implies treatment of the material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the material to be thermally diffused, and ion-implantation of the dopant into the semiconductor material.

When electrons are used as carriers, suitable dopants are for example halogens (e.g., $I_2$, $Cl_2$, $Br_2$, ICl, $ICl_3$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids or amino acids (e.g., HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Br), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the compounds and materials of the present invention can be used as an organic "metal" in applications, for example, but not limited to, charge injection layers and ITO planarising layers in organic light emitting diode applications, films for flat panel displays and touch screens, antistatic films, printed conductive substrates, patterns or tracts in electronic applications such as printed circuit boards and condensers.

These materials are particularly useful as semiconductors or charge transport materials, as they can be aligned into uniform highly ordered orientation in their liquid crystal phase by known techniques, thus exhibiting a higher degree of order that leads to particularly high charge carrier mobility. The highly ordered liquid-crystal state can be fixed by in situ polymerisation or crosslinking via the groups P to yield polymer films with high charge carrier mobility and high thermal, mechanical and chemical stability.

The oxadiazole derivatives, liquid-crystalline mixtures, polymerizable materials and/or polymer materials of the present invention are useful as optical, electronic and semiconductor materials, in particular as charge transport materials in field effect transistors (FETs), e.g., as components of integrated circuitry, ID tags or TFT applications. Such FETs, where an organic semiconductive material is arranged as a film between a gate-dielectric and a drain and a source electrode, are generally known, e.g., from U.S. Pat. No. 5,892,244, WO 00/79617 A1, U.S. Pat. No. 5,998,804, and from the references cited in the background and prior art chapter and listed below.

In security applications, field effect transistors and other devices with semiconductive materials, like transistors or diodes, may be used for ID tags or security markings to authenticate and prevent counterfeiting of documents of value like banknotes, credit cards or ID cards, national ID documents, licenses or any product with money value, like stamps, tickets, shares, cheques etc.

Especially the oligomeric and polymeric material according to the invention showing solubility properties allow production processes using solutions of these compounds. Thus films, including layers and coatings, may be generated by low cost production techniques, e.g. spin coating. Suitable solvents or solvent mixtures comprise alkanes and/or aromatics, especially their fluorinated derivatives.

Alternatively, the oxadiazole derivatives, liquid-crystalline mixtures, polymerizable materials and/or polymer materials of the present invention may be used in organic light emitting devices or diodes (OLEDs), e.g. in display applications or as backlight of, e.g., liquid-crystal displays. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The inventive compounds, materials and mixtures may be employed in one or more of the charge transport layers and/or in the emission layer, corresponding to their electrical and/or optical properties. The selection, characterization as well as the processing of suitable monomeric, oligomeric and polymeric compounds or materials for the use in OLEDs is generally known by a person skilled in the art, see, e.g., Meerholz, Synthetic Materials, 111–112, 2000, 31–34, Alcala, J. Appl. Phys., 88, 2000, 7124–7128 and the literature cited therein.

According to another use, the inventive compounds, materials or mixtures, especially those which show luminescent properties, may be employed as materials of light sources, e.g. of display devices such as described in EP 0 889 350 A1 or by C. Weder et al., Science, 279,1998, 835–837. Furthermore, they may be used in an electrooptic color display e. g. according to U.S. Pat. No. 4,822,144 or WO 00/57239 A1, where a backlight, switching elements and a luminescent pattern are combined.

Furthermore, the inventive compounds, mixtures and materials may be used as photovoltaic or sensor materials, for electrophotographic recording, and for other semiconductor applications.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding European Application No. 01129306.5, filed Dec. 13, 2001 is hereby incorporated by reference.

In the foregoing and in the following the abbreviation, listed below, are used:

| DCC | dicyclohexylcarbodiimide |
| LDA | lithiumdiisopropylamide |
| n-BuLi | n-butyllithium |
| THF | tetrahydrofuran |

EXAMPLES

The following examples are set forth to further illustrate the present invention and should not be construed as limiting the spirit or scope of the invention.

1. Synthesis of the Oxadiazole Derivative (6)

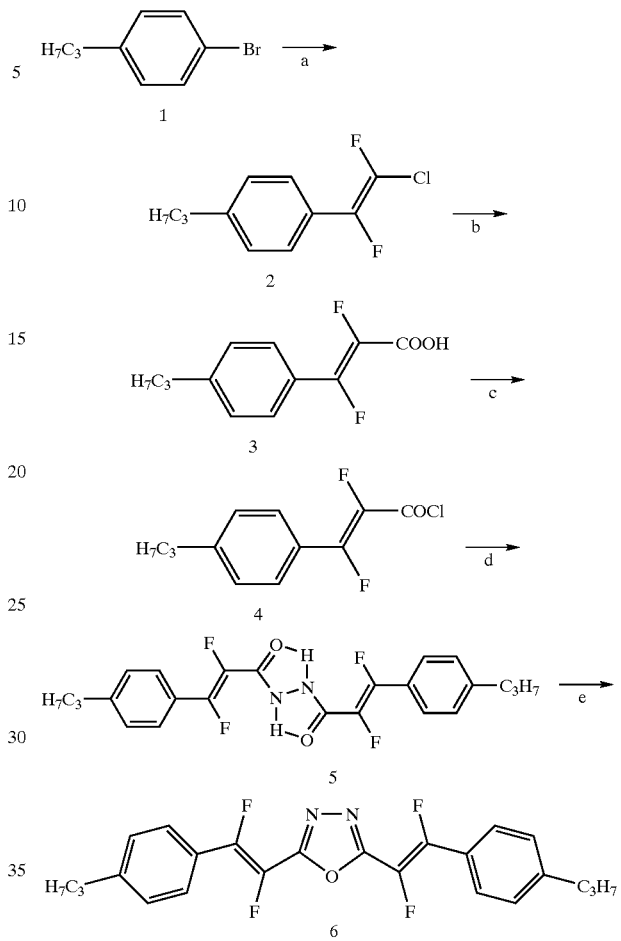

a) 1. Mg, THF; 2. $CF_2$=CFCl, from -40° C. to 20° C.. b) 1. BuLi, n-pentane, $Et_2O$, -100° C.; 2. $CO_2$. c) $SOCl_2$. d) $N_2H_4 \cdot H_2O$, THF. e) $POCl_3$.

1.1 Synthesis of the Styrene Derivative (2)

1.26 mol Mg in 1.8 l tetrahydrofuran (THF) were heated to 45° C. Approximately 10% of a solution of 1.25 mol p-bromo-propylbenzene (1) in 200 ml THF were added dropwise. After the starting of the Grignard reaction, the rest of the solution was added dropwise. The reaction mixture was stirred for 3 h at 50° C. Afterwards, the reaction mixture was cooled to −40° C. and 1.72 mol chloro-trifluoroethylene were passed into. The reaction mixture was stirred for 2 h at −35° C. and for about 10 h at 20° C. The mixture was brought into an ice/HCl mixture and extracted with methyl-tert-butylether (MTB) three times. The organic phases were worked up conventionally.

1.2 Synthesis of the Cinnamic Acid Derivative (3)

0.98 mol butyllithium (15% solution in n-pentane) were added dropwise into a solution of 0.98 mol of the styrene derivative 2 in a mixture of 630 ml THF, 350 ml diethylether and 350 ml n-pentane. After stirring for 1.5 h, the reaction mixture was brought into a suspension of 1 kg solid carbon dioxide in 1 l diethylether. The reaction mixture was brought to 20° C. slowly and acidified with 500 ml diluted aqueous HCl solution. The organic phase was worked up conventionally.

1.3 Synthesis of the Cinnamic Acid Chloride Derivative (4)

1.4 mol thionylchloride were added to 0.41 mol of the cinnamic acid derivative 3. After stirring for 15 min at 20° C., the reaction mixture was refluxed for 2 h. Afterwards, the excess thionylchloride was removed by distillation.

1.4 Synthesis of the Dimer (5)

0.025 mol hydrazinium hydroxide were added dropwise to a solution of 0.05 mol of the carbon acid chloride 4 in 250 ml 1,4-dioxane and 80 ml THF at 0° C. The reaction mixture was stirred for 30 min at 20° C. Subsequently 0.125 mol of a bortrifluoride ethylether complex in 25 ml 1,4-dioxane were added dropwise within 15 min. The product was hydrolyzed in a water/ice mixture and worked up conventionally to yield the dimer 5.

1.5 Synthesis of the Oxadiazole Product (6)

0.11 mol phosphorylchloride were added dropwise to 5.1 mmol of the dimer 5. After refluxing for 2 h the reaction mixture was poured onto ice, hydrolyzed and extracted with dichloromethan, followed by a conventional work up to yield the oxadiazole derivative 6 showing a blue fluorescence.

Experimental Data:
MS(EI): m/z=430 (M$^+$)
$^{19}$F-NMR (CDCl$_3$): δ=−138.9 (d, J=125 Hz, 2F), −167.9 (d, J=125 Hz, 2F).
UV (0.5 mg/100 ml CH$_3$CN): 227 nm, 279 nm, 329 nm.

2. Synthesis of the Polymerizable Oxadiazole Derivative (15)

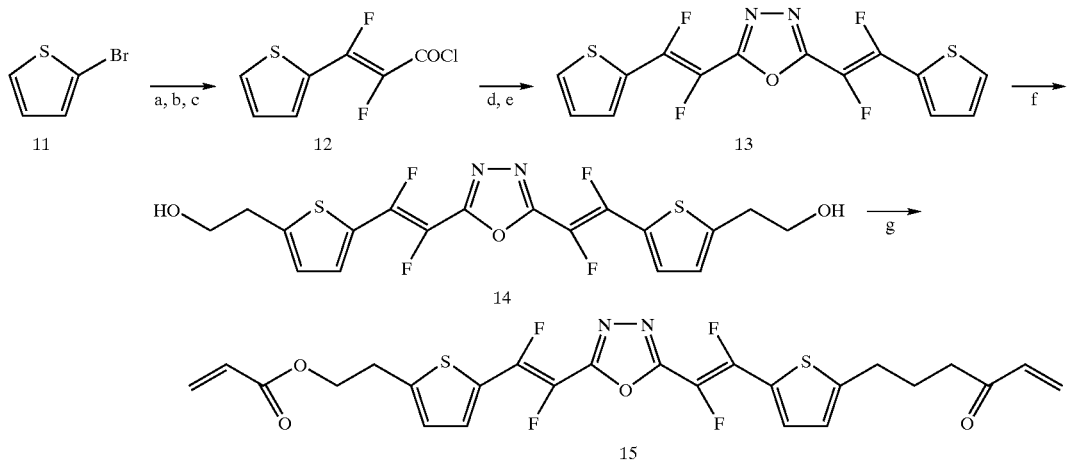

a) 1. Mg, THF; 2. CF$_2$=CFCl, from −40° C. to 20° C.. b) 1. BuLi, n-pentane, Et$_2$O, −100° C.; 2. CO$_2$. c) SOCl$_2$. d) N$_2$H$_4$·H$_2$O, THF. e) POCl$_3$. f) 1. LDA, THF; 2. ethylene oxide, from −40° C. to 20° C.. g) acrylic acid, DCC, THF.

2.1 Synthesis of the Carboxylic Acid Chloride (12) and of the Oxadiazole Compound (13)

The carboxylic acid chloride (12) is obtainable by applying the method described in the synthesis steps 1.1 to 1.3 as described above. Also the oxadiazole compound (13) can be synthesized in accordance with the method described in the synthesis steps 1.4 and 1.5.

2.2 Synthesis of the Oxadiazole Compound (14)

A solution of 20 mmol of the compound 13 in 200 ml THF is treated at −30° C. with 42 mmol LDA (1 M solution in THF) for 1 h. Then 45 mmol ethylene oxide are passed through the solution which is allowed to warm up to about 20° C. After stirring over night, the mixture is worked up as usual.

2.3 Synthesis of the Polymerizable Oxadiazole Derivative (15)

A solution of 10 mmol of the compound 14, 20 mmol of acrylic acid and 20 mmol of dicyclohexylcarbodiimide (DCC) in THF is stirred at about 20° C. for 10 h. The mixture is filtrated and evaporated to dryness. The residue is chromatographed.

Methacrylate derivatives are obtainable in analogy to the above described example.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. An oxadiazole compound comprising one or more identical or different recurring units of formula I

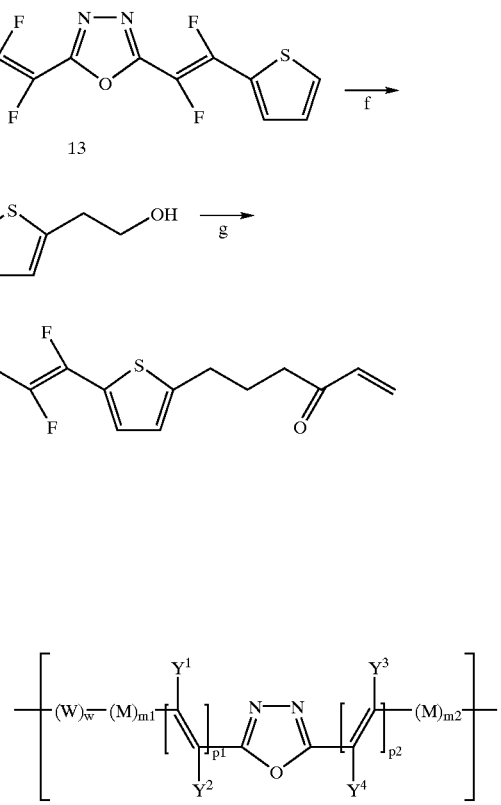

wherein
W is a straight chain or branched alkylene group with 1 to 22 C-atoms, which is unsubstituted or is mono- or polysubstituted by F, Cl, Br, I or CN, wherein one or more CH$_2$ groups may optionally be replaced, in each case independently from one another, by —O—, —S—, —NH—, —NR$^0$—, —CO—, —COO—, —OCO—, —OCO—O—, —S—CO—, —CO—S—, —CH=CH—, —CF=CF— or —C≡C— in such a manner that N, O and/or S atoms are not linked directly to one another;

$R^0$ is in each case independently H or alkyl with 1 to 12 C-atoms;

M is, if occuring twice or more, independently of each other, a mesogenic or mesogenity supporting group;

$Y^1$ to $Y^4$ are in each case independently of each other H, F, Cl or CN;

w is in each case independently 0 or 1;

m1, m2 are in each case independently and independently of each other 0 or 1, whereby m1+m2≧1; and p1, p2 are in each case independently and independently of each other 0 or 1, whereby p1+p2≧1;

wherein p1 is 1 and at least one of the substituents $Y^1$ and $Y^2$ is, independently, F, Cl or CN, p2 is 1 and at least one of the substituents $Y^3$ $Y^4$ is independently F, Cl or CN, or p1 is 1, p2 is 1, at least one of the substituents $Y^1$ and $Y^2$ is, in independently, F, Cl or CN, and at least one of the substituents $Y^3$ and $Y^4$ is, independently, F, Cl or CN.

2. An oxadiazole compound according to claim 1, wherein said compound is of formula I1

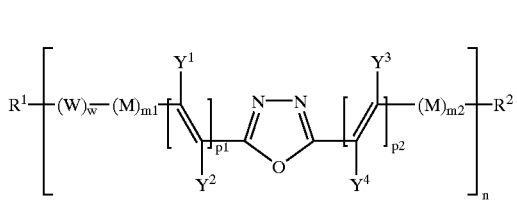

I1 wherein $R^1$, $R^2$ are independently of each other H, halogen, —NO$_2$, —CN, —NCS, optionally substituted aryl, optionally substituted heteroaryl, optionally substituted arylamino, P—Sp—X, or a straight chain, branched or cyclic alkyl with 1 to 20 C-atoms, which is unsubstituted or is mono- or polysubstituted by F, Cl, Br, I or CN, wherein one or more CH$_2$ groups may optionally be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N, O and/or S atoms are not linked directly to one another;

P is a polymerizable group;

Sp is a spacer group or a single bond;

X is —O—, —S—, —OCH$_2$—, —CH$_2$O—, —CO—, —COO—, —OCO—, —OCO—O—, —CO—NR$^0$—, —NR$^0$—CO—, —OCH$_2$—, —CH$_2$O—, —SCH$_2$—, —CH$_2$S—, —CH=CH—COO—, —OOC—CH=CH— or a single bond;

$R^0$, $R^{00}$ are independently of each other H or alkyl with 1 to 12 C-atoms; and n is 1, 2 or greater than 2.

3. An oxadiazole compound according to claim 2, wherein P is CH$_2$=CW$^1$—COO—,

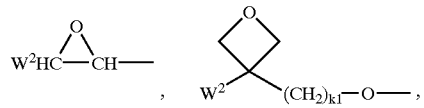

CH$_2$=CW$^2$—O—, CH$_3$—CH=CH—O—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$-Phe-(O)$_{k2}$—, Phe-CH=CH—, HOOC—, OCN— or W$^4$W$^5$W$^6$Si—;

$W^1$ is H, Cl, CN, phenyl or alkyl with 1 to 5 C-atoms;

$W^2$ and $W^3$ are each independently H or alkyl with 1 to 5 C-atoms;

$W^4$, $W^5$ and $W^6$ are each independently Cl, oxaalkyl or oxacarbonylalkyl with 1 to 5 C-atoms;

Phe is 1,4-phenylene;

k1 and k2 are each independently of each other 0 or 1; and

Sp is a linear or branched alkylene group having 1 to 20 C-atoms, wherein one or more non-adjacent CH$_2$ groups may optionally be replaced by —O—, —S—, —NH—, —N(CH$_3$)—, —CO—, —O—CO—, —S—CO—, —O—COO—, —CO—S—, —CO—O—, —CH(halogen)-, —C(halogen)$_2$, —CH(CN)—, —CH=CH—, —C≡C— or a siloxane group.

4. An oxadiazole compound according to claim 3, wherein M is a group of formula I2

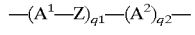

I2 wherein $A^1$, $A^2$ are independently of each other an aromatic group, a heteroaromatic group, or a saturated or partially saturated alicyclic or heterocyclic group, in each case having up to 25 C-atoms, and in each case being unsubstituted or mono- or polysubstituted by L, L is, if occuring twice or more, independently of each other, F, Cl, CN, alkyl with 1 to 6 C-atoms which is optionally mono- or polysubstituted by F, or alkoxy with 1 to 6 C-atoms which is optionally mono- or polysubstituted by F, Z is in each case independently —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$, —CL=CL—, —C≡C—, —CH=CH—COO—, —OCO—CH=CH— or a single bond, $R^0$ is in each case independently H or alkyl with 1 to 12 C-atoms, q1, q2 are in each case independently of each other 0, 1 or 2, whereby q1+q2≧1.

5. An oxadiazole compound according to claim 4, wherein $A^1$, $A^2$ are independently of one another a) trans-1,4-cyclohexylene, in which, in addition, one or more non-adjacent CH$_2$ groups are optionally replaced by —O— and/or —S—, b) a radical selected from 1,4-cyclohexenylene, 1,4-bicyclo[2.2.2]octylene, piperidine-1,4-diyl, decahydronaphthalene-2,6-diyl and 1,2,3,4-tetrahydro-naphthalene-2,6-diyl, c) 1,4-phenylene, in which, in addition, one or two CH groups are optionally replaced by N,
d) a radical selected from naphthalene-2,6-diyl, phenanthrene-diyl and anthracene-2,6-, -2,7- and -9,10-diyl, wherein, in each case, one or two CH groups are optionally replaced by N, or
e) a radical selected from furane, thiophene, thiophene-S,S-dioxide, oxazole, oxadiazole, pyrrole, imidazole, thiazole, thiadiazole-2,4- and -2,5-diyl, in which the radicals of the groups a), b), c), d) and e) are unsubstituted or mono- or polysubstituted by L, and L is, if occuring twice or more, independently of each other, F, Cl, CN, alkyl with 1 to 6 C-atoms which is unsubstituted or mono- or polysubstituted by F, or alkoxy with 1 to 6 C-atoms which is unsubstituted or mono- or polysubstituted by F.

6. An oxadiazole compound according to claim 2, wherein M is a group of formula I2

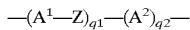   I2 wherein
$A^1, A^2$ are independently of each other an aromatic group, a heteroaromatic group, or a saturated or partially saturated alicyclic or heterocyclic group, in each case having up to 25 C-atoms, and in each case being unsubstituted or mono- or polysubstituted by L, L is, if occuring twice or more, independently of each other, F, Cl, CN, alkyl with 1 to 6 C-atoms which is optionally mono- or polysubstituted by F, or alkoxy with 1 to 6 C-atoms which is optionally mono- or polysubstituted by F, Z is in each case independently —O—, —S—, —CO—, —COO—, —OCO—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CL=CL—, —C≡C—, —CH=CH—COO—, —OCO—CH=CH— or a single bond, $R^0$ is in each case independently H or alkyl with 1 to 12 C-atoms, q1, q2 are in each case independently of each other 0, 1 or 2, whereby q1+q2≧1.

7. An oxadiazole compound according to claim 6, wherein $A^1, A^2$ are independently of one another
a) trans-1,4-cyclohexylene, in which, in addition, one or more non-adjacent CH$_2$ groups are optionally replaced by —O— and/or —S—,
b) a radical selected from 1,4-cyclohexenylene, 1,4-bicyclo[2.2.2]octylene, piperidine-1,4-diyl, decahydronaphthalene-2,6-diyl and 1,2,3,4-tetrahydronaphthalene-2,6-diyl,
c) 1,4-phenylene, in which, in addition, one or two CH groups are optionally replaced by N,
d) a radical selected from naphthalene-2,6-diyl, phenanthrene-diyl and anthracene-2,6-, -2,7- and -9,10-diyl, wherein, in each case, one or two CH groups are optionally replaced by N, or
e) a radical selected from furane, thiophene, thiophene-S,S-dioxide, oxazole, oxadiazole, pyrrole, imidazole, thiazole, thiadiazole-2,4- and -2,5-diyl, in which the radicals of the groups a), b), c), d) and e) are unsubstituted or mono- or polysubstituted by L, and L is, if occuring twice or more, independently of each other, F, Cl, CN, alkyl with 1 to 6 C-atoms which is unsubstituted or mono- or polysubstituted by F, or alkoxy with 1 to 6 C-atoms which is unsubstituted or mono- or polysubstituted by F.

8. An oxadiazole compound according to claim 2, wherein one or both of $R^1$ and $R^2$ is P—Sp—X.

9. An oxadiazole compound according to claim 8, wherein P is CH$_2$=CW$^1$—COO—,

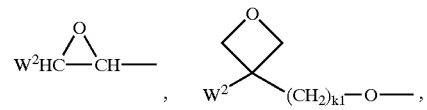

CH$_2$=CW$^2$—O—, CH$_3$—CH=CH—O—, HO—CW$^2$W$^3$, HS—CW$^2$W$^3$—, HW$^2$N—, HO—CW$^2$W$^3$—NH—, CH$_2$=CW$^1$—CO—NH—, CH$_2$=CH—(COO)$_{k1}$—Phe-(O)$_{k2}$—, Phe-CH=CH—, HOOC—, OCN— or W$^4$W$^5$W$^6$Si—;

$W^1$ is H, Cl, CN, phenyl or alkyl with 1 to 5 C-atoms;
$W^2$ and $W^3$ are each independently H or alkyl with 1 to 5 C-atoms;
$W^4$, $W^5$ and $W^6$ are each independently Cl, oxaalkyl or oxacarbonylalkyl with 1 to 5 C-atoms;
Phe is 1,4-phenylene; and
k1 and k2 are each independently of each other 0 or 1.

10. An oxadiazole compound according to claim 2, wherein if a p1 is 1, then at least one of the corresponding substituents $Y^1, Y^2$ is F, Cl or CN.

11. An oxadiazole compound according to claim 2, wherein if a p2 is 1, then at least one of the corresponding substituents $Y^3, Y^4$ is F, Cl or CN.

12. An oxadiazole compound according to claim 2, wherein if a p1 is 1, then both corresponding substituents $Y^1$ and $Y^2$ are independently of each other F, Cl or CN.

13. An oxadiazole compound according to claim 12, wherein both substituents $Y^1$ and $Y^2$ are F.

14. An oxadiazole compound according to claim 2, wherein if a p2 is 1, then both corresponding substituents $Y^3$ and $Y^4$ are independently of each other F, Cl or CN.

15. An oxadiazole compound according to claim 14, wherein both substituents $Y^3$ and $Y^4$ are F.

16. An oxadiazole compound according to claim 2, wherein at least one of $R^1$ and $R^2$ is $C_1$–$C_{12}$-alkyl, $C_2$–$C_{12}$-alkenyl or $C_1$–$C_{12}$-alkoxy, which in each case is optionally substituted with one or more fluorine atoms.

17. An oxadiazole compound according to claim 2, wherein $R^1, R^2$ are independently of each other H; halogen; —NO$_2$; —CN; —NCS;

aryl optionally substituted with one or more of halogen, —NO$_2$, —CN, —NCS, straight chain, branched or cyclic alkyl with 1–20 C atoms, which is unsubstituted mono-, or polysubstituted by F, Cl, Br, I, or CN and in which one or more adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, CO—S—, —CH=CH— or —C≡C— in such a manner that N,O and/or S atoms are not linked directly to one another, heteroaryl optionally substituted with one or more of halogen, —NO$_2$, —CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or C≡C— in such a manner that N,O and/or atoms are not linked directly to one another;

arylamino wherein the aryl group is optionally substituted with one or more of halogen, —NO$_2$,—CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or —C≡C— in such a matter that N,O and/or S atoms are not linked directly to one another, P—Sp—X, or a straight chain, branched or cyclic alkyl with 1 to 20 C-atoms, which is unsubstituted or is mono- or polysubstituted by F, Cl, Br, I or CN, wherein one or more $CH_2$ groups may optionally be replaced, in each case independently from one another, by —O—, —S—, —NH—, —NR$^o$—, —SiR$^o$R$^{oo}$—, —CO—, —COO—, —OCO—, —OCO—O—, —S—CO—, —CO—S—, —CH=CH— or —C≡C— in such a manner that N, O and/or S atoms are not linked directly to one another.

18. An oxadiazole compound according to claim 1, wherein M is a group of formula I2

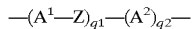

I2 wherein $A^1$, $A^2$ are independently of each other an aromatic group, a heteroaromatic group, or a saturated or partially saturated alicyclic or heterocyclic group, in each case having up to 25 C-atoms, and in each case being unsubstituted or mono- or polysubstituted by L, L is, if occuring twice or more, independently of each other, F, Cl, CN, alkyl with 1 to 6 C-atoms which is optionally mono- or polysubstituted by F, or alkoxy with 1 to 6 C-atoms which is optionally mono- or polysubstituted by F, Z is in each case independently —O—, —S—, —CO—, —COO—, —OCO—, —O—COO—, —CO—NR$^o$, —NR$^o$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^o$—, —CL=CL—, —C≡C—, —CH=CH—COO—, —OCO—CH=CH— or a single bond, R$^o$ is in each case independently H or alkyl with 1 to 12 C-atoms, q1, q2 are in each case independently of each other 0, 1 or 2, whereby q1+q2≧1.

19. An oxadiazole compound according to claim 18, wherein $A^1$, $A^2$ are independently of one another a) trans-1,4-cyclohexylene, in which, in addition, one or more non-adjacent $CH_2$ groups are optionally replaced by —O— and/or —S—, b) a radical selected from 1,4-cyclohexenylene, 1,4-bicyclo[2.2.2]octylene, piperidine-1,4-diyl, decahydronaphthalene-2,6-diyl and 1,2,3,4-tetrahydro-naphthalene-2,6-diyl, c) 1,4-phenylene, in which, in addition, one or two CH groups are optionally replaced by N, d) a radical selected from naphthalene-2,6-diyl, phenanthrene-diyl and anthracene-2,6-, -2,7- and -9,10-diyl, wherein, in each case, one or two CH groups are optionally replaced by N, or e) a radical selected from furane, thiophene, thiophene-S,S-dioxide, oxazole, oxadiazole, pyrrole, imidazole, thiazole, thiadiazole-2,4- and -2,5-diyl, in which the radicals of the groups a), b), c), d) and e) are unsubstituted or mono- or polysubstituted by L, and L is, if occuring twice or more, independently of each other, F, Cl, CN, alkyl with 1 to 6 C-atoms which is unsubstituted or mono- or polysubstituted by F, or alkoxy with 1 to 6 C-atoms which is unsubstituted or mono- or polysubstituted by F.

20. An oxadiazole compound according claim 1, wherein said compound is of formula II

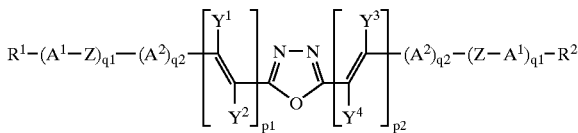

II wherein $R^1$, $R^2$ are independently of each other H, halogen, —NO$^2$, —CN, —NCS, optionally substituted aryl, optionally substituted heteroaryl, optionally substituted arylamino, P—Sp—X, or a straight chain, branched or cyclic alkyl with 1 to 20 C-atoms, which is unsubstituted or is mono- or polysubstituted by F, Cl, Br I or CN, wherein one or more $CH_2$ groups may optionally be replaced, in each case independently from one another, by —O—, —S—, —NH—, —NR$^o$—, —SiR$^o$R$^{oo}$—, —CO—, —COO—, —OCO—O—, —S—CO—, —CO—S—, —CH=CH— or —C≡— in such a manner that N, O and/or S atoms are not linked directly to one another;

$A^1$, $A^2$ are independently of each other an aromatic group, a heteroaromatic group, or a saturated or partially saturated alicyclic or heterocyclic group, in each case having up to 25 C-atoms, and in each case being unsubstituted or mono- or polysubstituted by L, L is, if occuring twice or more, independently of each other, F, Cl, CN, alkyl with 1 to 6 C-atoms which is optionally mono- or polysubstituted by F, or alkoxy with 1 to 6 C-atoms which is optionally mono- or polysubstituted by F, Z is in each case independently —O—, —S—, —CO—, —COO—, —OCO—, —O—COO—, —CO—NR$^o$—, —NR$^o$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^o$—, —CL=CL—, —C≡C—, —CH=CH—COO—, —OCO—CH=CH— or a single bond, R$^o$ is in each case independently H or alkyl with 1 to 12 C-atoms, and q1, q2 are in each case independently of each other 0, 1 or 2, whereby q1+q2≧1.

21. An oxadiazole compound according to claim 20, wherein $R^1$, $R^2$ are independently of each other H; halogen; —$NO_2$; —CN; —NCS;

aryl optionally substituted with one or more of halogen, —$NO_2$,—CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=CH— or —C≡C— in such a manner that N,O and/or S atoms are not linked directly to one another;

heteroaryl optionally substituted with one or more of halogen, —$NO_2$,—CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=CH— or —C≡C— in such a manner that N,O and/or S atoms are not linked directly to one another;

arylamino wherein the aryl group is optionally substituted with one or more of halogen, —$NO_2$,—CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=CH— or —C≡C— in such a manner that N,O and/or S atoms are not linked directly to one another, P—Sp—X, or a straight chain, branched or cyclic alkyl with 1 to 20 C-atoms, which is unsubstituted or is mono- or polysubstituted by F, Cl, Br, I or CN, wherein one or more $CH_2$ groups may optionally be replaced, in each case independently from one another, by —O—, —S—, —NH—, —$NR^o$—, —$SiR^oR^{oo}$—, —CO—, —COO—, —OCO—, —CO—O—, —S—CO—, —CO—S—, —CH=CH— or —C≡C— in such a manner that N, O and/or S atoms are not linked directly to one another.

22. An oxadiazole compound according to claim 20 wherein said oxadiazole compound is of formulae II.1 to II.22, and wherein each 1,4 phenylene group and each thiophenylene group is optionally substituted by 1 to substituents L, wherein s is 4 in the case of 1,4-phenylene and s is 2 in the case of thiophenylene:

II.1

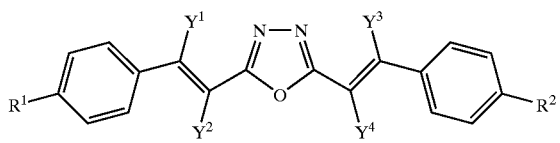

II.2

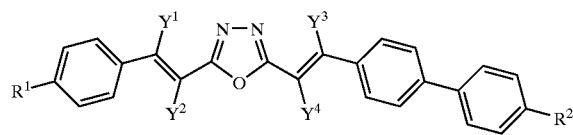

II.3

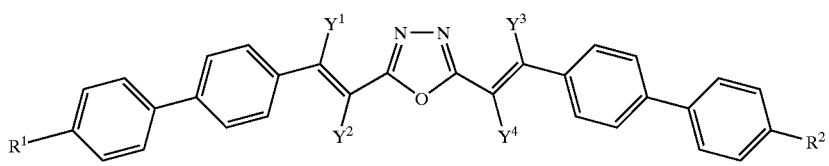

II.4

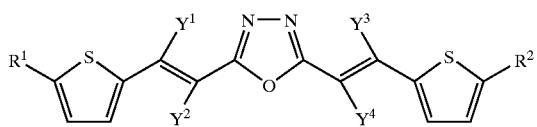

II.5

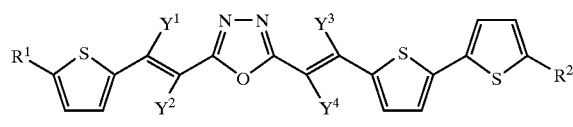

II.6

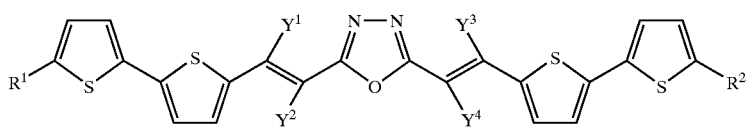

II.7

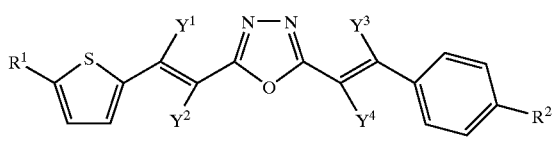

II.8

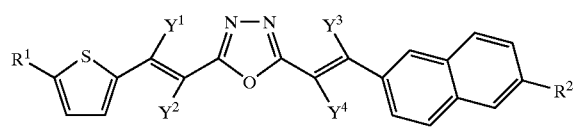

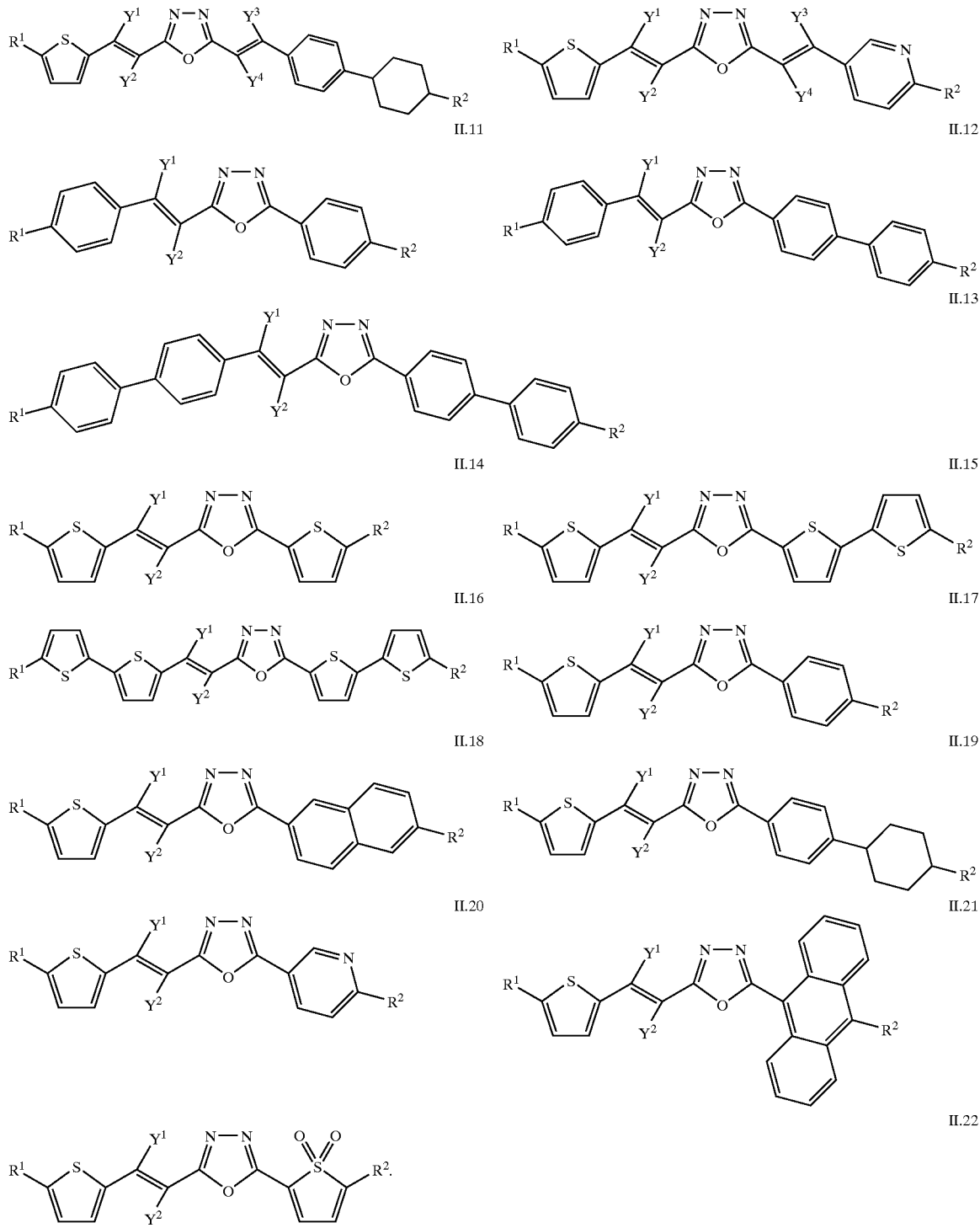

23. An oxadiazole compound according to claim 22, wherein $R^1$, $R^2$ are independently of each other H; halogen; —$NO_2$; —CN; —NCS;

aryl optionally substituted with one or more of halogen, —$NO_2$,—CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH=CH— or —C≡C— in such a manner that N,O and/or S atoms are not linked directly to one another;

heteroaryl optionally substituted with one or more of halogen, —$NO_2$,—CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=CH— or —C≡C— in such a manner that N,O and/or S atoms are not linked directly to one another;

arylamino wherein the aryl group is optionally substituted with one or more of halogen, —$NO_2$, —CN, —NCS, straight chain, branched or cyclic alkyl with 1–20 C atoms, which is unsubstituted mono-, or polysubstituted by F, Cl, Br, I, or CN and in which one or more adjacent $CH_2$ groups can be replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=CH— or —C≡C— in such a manner that N,O and/or S atoms are not linked directly to one another, P—Sp—X, or a straight chain, branched or cyclic alkyl with 1 to 20 C-atoms, which is unsubstituted or is mono- or polysubstituted by F, Cl, Br, I or CN, wherein one or more $CH_2$ groups may optionally be replaced, in each case independently from one another, by —O—, —S—, —NH—, —$NR^o$—, —$SiR^oR^{oo}$—, —CO—, —COO—, —OCO—, —CO—O—, —S—CO—, —CO—S—, —CH=CH— or —C≡C— in such a manner that N, O and/or S atoms are not linked directly to one another.

24. An oxadiazole compound according to claim 1, wherein said compound is of formula III

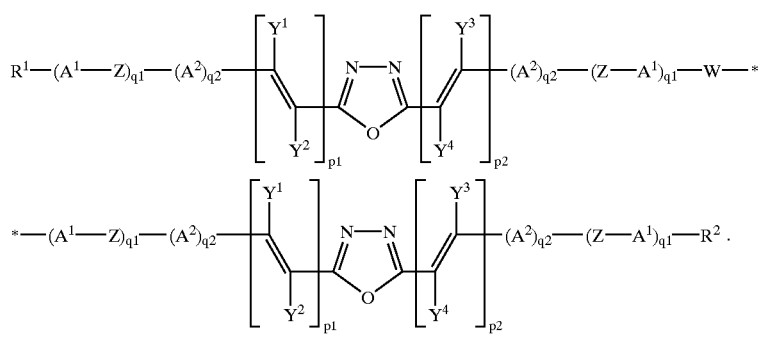

III wherein
$R^1$, $R^2$ are independently of each other H, halogen, —$NO_2$, —CN, —NCS, optionally substituted aryl, optionally substituted heteroaryl, optionally substituted arylamino, P—Sp—X, or a straight chain, branched or cyclic alkyl with 1 to 20 C-atoms, which is unsubstituted or is mono- or polysubstituted by F, Cl, Br, I or CN, wherein one or more $CH_2$ groups may optionally be replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —CH=CH— or —C≡C— in such a manner that N, O and/or S atoms are not linked directly to one another;

$A^1$, $A^2$ are independently of each other an aromatic group, a heteroaromatic group, or a saturated or partially saturated alicyclic or heterocyclic group, in each case having up to 25 C-atoms, and in each case being unsubstituted or mono- or polysubstituted by L, L is, if occuring twice or more, independently of each other, F, Cl, CN, alkyl with 1 to 6 C-atoms which is optionally mono- or polysubstituted by F, or alkoxy with 1 to 6 C-atoms which is optionally mono- or polysubstituted by F, Z is in each case independently —O—, —S—, —CO—, —COO—, —OCO—, —O—COO—, —CO—$NR^o$—, —$NR^o$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=$CR^o$—, —CL=CL—, —C≡C—, —CH=CH—COO—, —OCO—CH=CH— or a single bond, $R^o$ is in each case independently H or alkyl with 1 to 12 C-atoms, and q1, q2 are in each case independently of each other 0, 1 or 2, whereby q1+q2≧1.

25. An oxadiazole compound according to claim 24, wherein when an index p1 is 1, then at least one of the corresponding substituents $Y^1$ and $Y^2$ is F, Cl, or CN.

26. An oxadiazole compound according to claim 24, wherein when an index p2 is 1, then at least one of the corresponding substituents $Y^3$ and $Y^4$ is F, Cl, or CN.

27. An oxadiazole compound according to claim 24, wherein when an index p1 is 1, then both corresponding substituents $Y^1$ and $Y^2$ are independently of each other F, Cl, or CN.

28. An oxadiazole compound according to claim 24, wherein when an index p2 is 1, then both corresponding substituents $Y^3$ and $Y^4$ are independently of each other F, Cl, or CN.

29. An oxadiazole compound according to claim 24, wherein at least one of $R^1$ and $R^2$ is $C_1$–$C_{12}$-alkyl, $C_2$–$C_{12}$-alkenyl or $C_1$–$C_{12}$-alkoxy, which in each case is optionally substituted with one or more fluorine atoms.

30. An oxadiazole compound according to claim 24, wherein at least one of $R^1$ and $R^2$ is a polymerizable group P—Sp—X—.

31. An oxadiazole compound according to claim 24, wherein said oxadiazole compound is of formulae III.1 to III.6, wherein each 1,4-phenylene group and each thiophenylene group is optionally substituted by 1 to s substituents L, wherein s is 4 in the case of 1,4-phenylene and s is 2 in the case of thiophenylene:

III.1
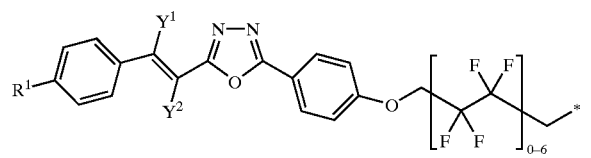

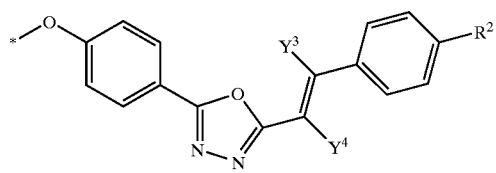

III.2
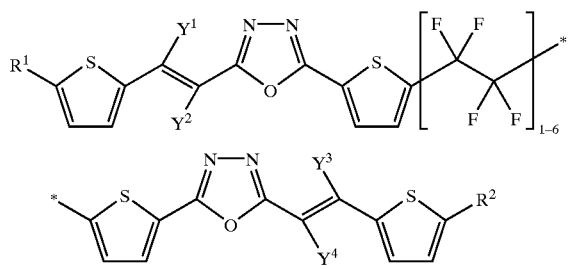

III.3
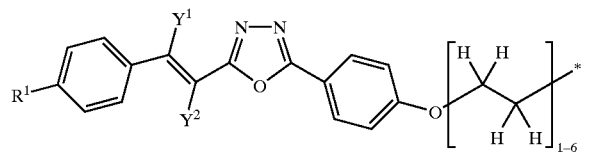

III.4
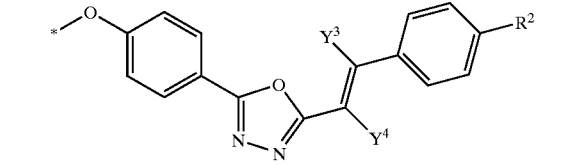

III.5
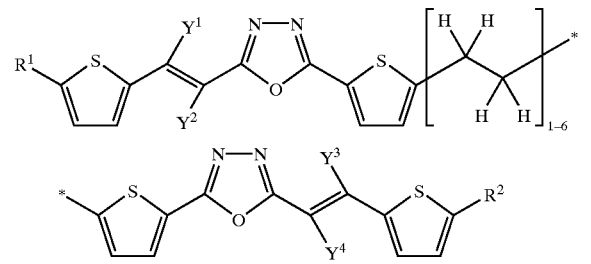

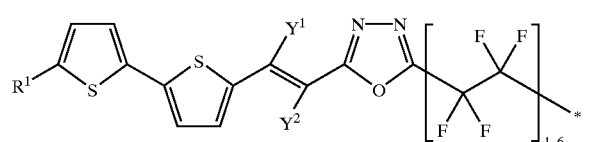

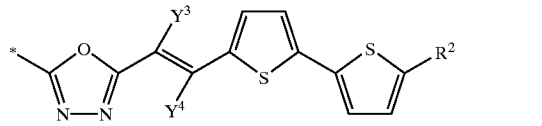

III.6
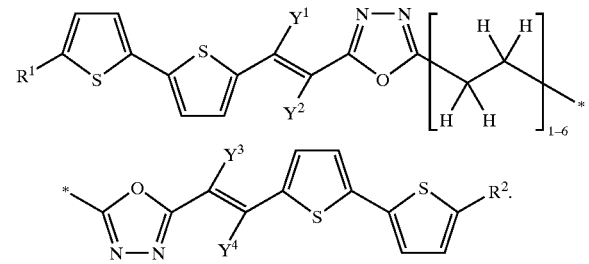

32. An oxadiazole compound according to claim 31, wherein $R^1$, $R^2$ are independently of each other H; halogen; —NO$_2$; —CN; —NCS;

aryl optionally substituted with one or more of halogen, —NO$_2$,—N, —NCS, straight chain, branched or cyclic alkyl with 1–20 C atoms, which is unsubstituted mono-, or polysubstituted by F, Cl, Br, I, or CN and in which one or more adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N,O and/or S atoms are not linked directly to one another;

heteroaryl optionally substituted with one or more of halogen, —NO$_2$,—CN, —NCS, straight chain, branched or cyclic alkyl with 1–20 C atoms, which is unsubstituted mono-, or polysubstituted by F, Cl, Br, I, or CN and in which one or more adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N,O and/or S atoms are not linked directly to one another;

arylamino wherein the aryl group is optionally substituted with one or more of halogen, —NO$_2$,—CN, —NCS, straight chain, branched or cyclic alkyl with 1–20 C atoms, which is unsubstituted mono-, or polysubstituted by F, Cl, Br, I, or CN and in which one or more adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N,O and/or S atoms are not linked directly to one another, P—Sp—X, or a straight chain, branched or cyclic alkyl with 1 to 20 C-atoms, which is unsubstituted or is mono- or polysubstituted by F, Cl, Br, I or CN, wherein one or more CH$_2$ groups may optionally be replaced, in each case independently from one another, by —O—, —S—, —NH—, —NR$^0$—, —SiR$^0$R$^{00}$—, —CO—, —COO—, —OCO—, —CO—O—, —S—CO—, —CO—S—, —CH=CH— or —C≡C— in such a manner that N, O and/or S atoms are not linked directly to one another.

33. An oxadiazole compound according to claim 24, wherein $R^1$, $R^2$ are independently of each other H; halogen; —NO$_2$; —CN; —NCS;

aryl optionally substituted with one or more of halogen, —NO$_2$, —CN, —NCS, straight chain, branched or cyclic alkyl with 1–20 C atoms, which is unsubstituted mono-, or polysubstituted by F, Cl, Br, I, or CN and in which one or more adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N,O and/or S atoms are not linked directly to one another;

heteroaryl optionally substituted with one or more of halogen, —NO$_2$,—CN, —NCS, straight chain, branched or cyclic alkyl with 1–20 C atoms, which is unsubstituted mono-, or polysubstituted by F, Cl, Br, I, or CN and in which one or more adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N,O and/or S atoms are not linked directly to one another;

arylamino wherein the aryl group is optionally substituted with one or more of halogen, —NO$_2$,—CN, —NCS, straight chain, branched or cyclic alkyl with 1–20 C atoms, which is unsubstituted mono-, or polysubstituted by F, Cl, Br, I, or CN and in which one or more adjacent CH$_2$ groups can be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N,O and/or S atoms are not linked directly to one another, P—Sp—X, or a straight chain, branched or cyclic alkyl with 1 to 20 C-atoms, which is unsubstituted or is mono- or polysubstituted by F, Cl, Br, I or CN, wherein one or more CH$_2$ groups may optionally be replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CH=CH— or —C≡C— in such a manner that N, O and/or S atoms are not linked directly to one another.

34. An oxadiazole compound according to claim 1, wherein W is a bridging group of formula I3

I3 wherein

Q$^1$, Q$^2$ are independently of each other —O—, —S—, —COO—, —OCO—, —CO— or a single bond;

R$^3$, R$^4$ are independently of each other H, F, Cl, CN, alkyl with 1 to 6 C-atoms which is unsubstituted or mono- or polysubstituted by F, or alkoxy with 1 to 6 C-atoms, which is unsubstituted or mono- or polysubstituted by F, and v is 1 to 20.

35. An oxadiazole compound according to claim 34, wherein v≧2.

36. An oxadiazole compound according to claim 34, wherein R$^3$, R$^4$ are independently of each other H or F.

37. An oxadiazole compound according to claim 34, wherein v≧4 and at least four substituents R$^3$, R$^4$ are F, and the other substituents R$^3$, R$^4$ are H.

38. An oxadiazole compound according to claim 34, wherein Q$^1$ and Q$^2$ are —O— or a single bond.

39. An oxadiazole compound according to claim 1, wherein p1 is 1 and substituents Y$^1$ and Y$^2$ are each F, p2 is 1 and substituents Y$^3$ and Y$^4$ are each F, or p1 is 1, p2 is 1, and substituents Y$^1$, Y$^2$, Y$^3$ and Y$^4$ are each F.

40. In a liquid-crystalline mixture comprising at least two components, at least one of which is liquid-crystalline, the improvement wherein said mixture contains at least one oxadiazole compound according to claim 1.

41. A liquid-crystalline mixture according to claim 40, wherein at least one component is polymerizable, crosslinkable or both.

42. A liquid-crystalline mixture according to claim 40, wherein said at least one oxadiazole compound is polymerizable, crosslinkable or both.

43. A polymeric material having charge transport properties, luminescent properties, or both, wherein said polymeric material is obtainable by polymerising and/or crosslinking a liquid-crystalline mixture according to claim 40.

44. A polymeric material according to claim 43, wherein said polymeric material exhibits anisotropic charge transport, luminescent properties, or both.

45. A polymeric material according to claim 44, wherein said oxadiazole compound is oxidatively or reductively doped to form a conducting ionic species.

46. A polymeric material according to claim 43, which is obtainable by:

a) forming a layer of the liquid-crystalline mixture, b) aligning molecules of the compounds of the mixture in the layer into a uniform orientation or a patterned orientation whereby in each pattern the orientation is uniform, c) polymerizing said liquid-crystalline mixture.

47. A polymerizable material according to claim 43, wherein said oxadiazole compound is oxidatively or reductively doped to form a conducting ionic species.

48. A liquid-crystalline mixture according to claim 40, wherein said oxadiazole compound is oxidatively or reductively doped to form a conducting ionic species.

49. A polymerizable material comprising one or more oxadiazole compounds according to claim 1 and optionally one or more further compounds, wherein at least one oxadiazole compound and/or at least one of said further compounds is polymerizable.

50. A polymerizable material according to claim 49, wherein at least one of the oxadiazole compounds is mesogenic or liquid-crystalline, and polymerizable, crosslinkable or both.

51. A polymerizable material according to claim 49, wherein said material contains one or more of said further compounds and at least one of said further compounds is polymerizable.

52. A polymeric material having charge transport properties, luminescent properties, or both, wherein said polymeric material is obtainable by polymerising and/or crosslinking a polymerizable material according to claim 49.

53. A polymeric material according to claim 52, wherein said polymeric material exhibits anisotropic charge transport, luminescent properties, or both.

54. An polymeric material according to claim 53, wherein said oxadiazole compound is oxidatively or reductively doped to form a conducting ionic species.

55. A polymeric material according to claim 52, which is obtainable by:
a) forming a layer of the polymerizable material,
b) aligning molecules of the compounds of the mixture in the layer into a uniform orientation or a patterned orientation whereby in each pattern the orientation is uniform,
c) polymerizing said polymerizable material.

56. A polymerizable material according to claim 52, wherein said oxadiazole compound is oxidatively or reductively doped to form a conducting ionic species.

57. An oxadiazole compound according to claim 1, wherein said oxadiazole compound is oxidatively or reductively doped to form a conducting ionic species.

58. In a method of preparing a liquid-crystalline mixture comprising combining components together, the improvement wherein at least one component is at least one oxadiazole compound according to claim 1.

59. In a method of manufacturing a semiconductor, charge transport, photo-conducting, photo-luminescent and/or electro-luminescent material containing at least one mesogenic or liquid crystalline compound, a liquid-crystalline mixture, a polymerizable material or a polymer, the improvement wherein at least one oxadiazole compound according to claim 1 is employed as the compound or is employed in the preparation of said liquid-crystalline mixture, said polymerizable material or said polymer.

60. In a semiconductor, charge transport, photo-conducting, photo-luminescent and/or electro-luminescent material, comprising at least one mesogenic or liquid crystalline compound, a liquid-crystalline mixture, a polymerizable material or a polymer, the improvement wherein at least one oxadiazole compound according to claim 1 is employed as the compound or is employed in the preparation of said liquid-crystalline mixture, said polymerizable material or said polymer.

61. In a field effect transistor, which may be a component of integrated circuitry, a thin film transistor in flat panel display applications, or in a Radio Frequency Identification (RFID) tag, comprising at least one mesogenic or liquid crystalline compound, a liquid-crystalline mixture, a polymerizable material or a polymer, the improvement wherein at least one oxadiazole compound is employed as the compound or is employed in the preparation of said liquid-crystalline mixture, said polymerizable material or said polymer, and said at least one oxadiazole compound comprises one or more identical or different recurring units of formula I

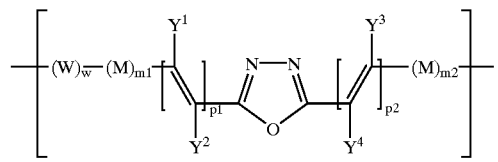

wherein
W is a straight chain or branched alkylene group with 1 to 22 C-atoms, which is unsubstituted or is mono- or polysubstituted by F, Cl, Br, I or CN, wherein one or more $CH_2$ groups may optionally be replaced, in each case independently from one another, by —O—, —S—, —NH—, —$NR^0$—, —CO—, —COO—, —OCO—, —OCO—O—, —S—CO—, —CO—S—, —CH=CH—, —CF=CF— or —C≡C— in such a manner that N, O and/or S atoms are not linked directly to one another;

$R^0$ is in each case independently H or alkyl with 1 to 12 C-atoms;

M is, if occuring twice or more, independently of each other, a mesogenic or mesogenity supporting group;

$Y^1$ to $Y^4$ are in each case independently of each other H, F, Cl or CN;

w is in each case independently 0 or 1;

m1, m2 are in each case independently and independently of each other 0 or 1, whereby m1+m2≧1; and p1, p2 are in each case independently and independently of each other 0 or 1, whereby p1+p2≧1;

with the proviso that formula I does not include 2-styryl-5-trichloromethyl-oxadiazole, 2-styryl-5-tribromomethyl-oxadiazole, 2-(alkylstyryl)-5-trichloromethyl-oxadiazole, 2-(alkylstyryl)-5-tribromethyl-oxadiazole, 2-(alkoxystyryl)-5-trichloromethyl-oxadiazole, 2-(alkoxystyryl)-5-tribromomethyl-oxadiazole, 2-(4-chlorostyryl)-5-trichloromethyl-oxadiazole, 2-(4-chlorostyryl)-5-tribromomethyl-oxadiazole, 2-(4-styrylstyryl)-5-trichloromethyl-oxadiazole, 2-(4-styrylstyryl)-5-tribromomethyl-oxadiazole, 2-(benzofuran-2-yl)-5-trichloromethyl-oxadiazole, and 2-(benzofuran-2-yl)-5-tribromomethyl-oxadiazole.

62. In a security marking or device comprising at least one mesogenic or liquid crystalline compound, a liquid-crystalline mixture, a polymerizable material or a polymer, the improvement wherein at least one oxadiazole compound is employed as the compound or is employed in the preparation of said liquid-crystalline mixture, said polmerizable material or said polymer, and said at least one oxadiazole compound comprises one or more identical or different recurring units of formula I

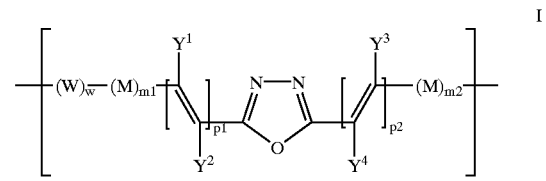

wherein
W is a straight chain or branched alkylene group with 1 to 22 C-atoms, which is unsubstituted or is mono- or polysubstituted by F, Cl, Br, I or C wherein one or more $CH_2$ groups may optionally be replaced, in each case in independently from one another, by —O—, —S—, —NH—, —$NR^0$—, —CO—, —COO—, —OCO—, —OCO—O—, —S—CO—, —CO—S—, —CH=CH—, —CF=CF— or —C≡C— in such a manner that N, O and/or S atoms are not linked directly to one another;

$R^0$ is in each case independently H or alkyl with 1 to 12 C-atoms;

M is, if occuring twice or more, independently of each other, a mesogenic or mesogenity supporting group;

$Y^1$ to $Y^4$ are in each case independently of each other H, F, Cl or CN;

w is in each case independently 0 or 1;

m1, m2 are in each case independently and independently of each other 0 or 1, whereby m1+m2≧1; and p1, p2 are in each case independently and independently of each other 0 or 1, whereby p1+p2≧1;

with the proviso that formula I does not include
2-styryl-5-trichloromethyl-oxadiazole, 2-styryl-5-tribromomethyl-oxadiazole, 2-(alkylstyryl)-5-trichloromethyl-oxadiazole, 2-(alkylstyryl)-5-tribromomethyl-oxadiazole, 2-(alkoxystyryl)-5-trichloromethyl-oxadiazole, 2-(alkoxystyryl)-5-tribromomethyl-oxadiazole, 2-(4-chlorostyryl)-5-tribromomethyl-oxadiazole, 2-(4-chlorostyryl)-5-tribromomethyl-oxadiazole, 2-(4-styrylstyryl)-5-trichloromethyl-oxadiazole, 2-(4-styrylstyryl)-5-tribromomethyl-oxadiazole, 2-(benzofuran-2-yl)-5-trichloromethyl-oxadiazole, and 2-(benzofuran-2-yl)-5-tribromomethyl-oxadiazole.

63. In a charge injection layer, planarising layer, antistatic film or conducting substrate or pattern for electronic applications or flat panel displays, comprising at least one mesogenic or liquid crystalline compound, a liquid-crystalline mixture, a polymerizable material or a polymer, the improvement wherein at least one oxadiazole compound is employed as the compound or is employed in the preparation of said liquid-crystalline mixture, said polymerizable material or said polymer, and said at least one oxadiazole compound comprises one or more identical or different recurring units of formula I

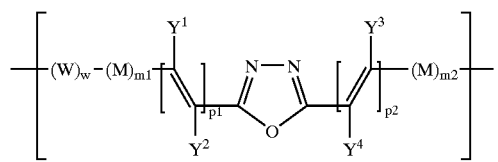

wherein

W is a straight chain or branched alkylene group with 1 to 22 C-atoms, which is unsubstituted or is mono- or polysubstituted by F, Cl, Br, I or C wherein one or more $CH_2$ groups may optionally be replaced, in each case in independently from one another, by —O—, —S—, —NH—, —NR$^O$—, —CO—, —COO—, —OCO—, —OCO—O—, —S—CO—, —CO—S—, —CH=CH—, —CF=CF— or —C≡C— in such a manner that N, O and/or S atoms are not linked directly to one another;

$R^O$ is in each case independently H or alkyl with 1 to 12 C-atoms;

M is, if occuring twice or more, independently of each other, a mesogenic or mesogenity supporting group;

$Y^1$ to $Y^4$ are in each case independently of each other H, F, Cl or CN;

w is in each case independently 0 or 1;

m1, m2 are in each case independently and independently of each other 0 or 1, whereby m1+m2≧1; and p1, p2 are in each case independently and independently of each other 0 or 1, whereby p1+p2≧1;

with the proviso that formula I does not include
2-styryl-5-trichloromethyl-oxadiazole, 2-styryl-5-tribromomethyl-oxadiazole, 2-(alkylstyryl)-5-trichloromethyl-oxadiazole, 2-(alkylstyryl)-5-tribromomethyl-oxadiazole, 2-(alkoxystyryl)-5-trichloromethyl-oxadiazole, 2-(alkoxystyryl)-5-tribromomethyl-oxadiazole, 2-(4-chlorostyryl)-5-tribromomethyl-oxadiazole, 2-(4-chlorostyryl)-5-tribromomethyl-oxadiazole, 2-(4-styrylstyryl)-5-trichloromethyl-oxadiazole, 2-(4-styrylstyryl)-5-tribromomethyl-oxadiazole, 2-(benzofuran-2-yl)-5-trichloromethyl-oxadiazole, and 2-(benzofuran-2-yl)-5-tribromomethyl-oxadiazole.

64. In a liquid-crystal display element comprising at least one mesogenic or liquid crystalline compound, a liquid-crystalline mixture, a polymerizable material or a polymer, the improvement wherein at least one oxadiazole compound is employed as the compound or is employed in the preparation of said liquid-crystalline mixture, said polymerizable material or said polymer, and said at least one oxadiazole compound comprises one or more identical or different recurring units of formula I

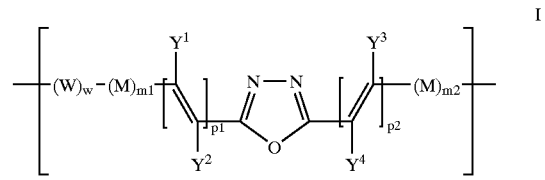

wherein

W is a straight chain or branched alkylene group with 1 to 22 C-atoms, which is unsubstituted or is mono- or polysubstituted by F, Cl, Br, I or C wherein one or more $CH_2$ groups may optionally be replaced, in each case in independently from one another, by —O—, —S—, —NH—, —NR$^O$—, —CO—, —COO—, —OCO—, —OCO—O—, —S—CO—, —CO—S—, —CH=CH—, —CF=CF— or —C≡C— in such a manner that N, O and/or S atoms are not linked directly to one another;

$R^O$ is in each case independently H or alkyl with 1 to 12 C-atoms;

M is, if occuring twice or more, independently of each other, a mesogenic or mesogenity supporting group;

$Y^1$ to $Y^4$ are in each case independently of each other H, F, Cl or CN;

w is in each case independently 0 or 1;

m1, m2 are in each case independently and independently of each other 0 or 1, whereby m1+m2≧1; and p1, p2 are in each case independently and independently of each other 0 or 1, whereby p1+p2≧1;

with the proviso that formula I does not include
2-styryl-5-trichloromethyl-oxadiazole, 2-styryl-5-tribromomethyl-oxadiazole, 2-(alkylstyryl)-5-trichloromethyl-oxadiazole, 2-(alkylstyryl)-5-tribromomethyl-oxadiazole, 2-(alkoxystyryl)-5-trichloromethyl-oxadiazole, 2-(alkoxystyryl)-5-tribromomethyl-oxadiazole, 2-(4-chlorostyryl)-5-tribromomethyl-oxadiazole, 2-(4-chlorostyryl)-5-tribromomethyl-oxadiazole, 2-(4-styrylstyryl)-5-trichloromethyl-oxadiazole, 2-(4-styrylstyryl)-5-tribromomethyl-oxadiazole, 2-(benzofuran-2-yl)-5-trichloromethyl-oxadiazole, and 2-(benzofuran-2-yl)-5-tribromomethyl-oxadiazole.

65. An oxadiazole compound comprising one or more identical or different recurring units of formula I

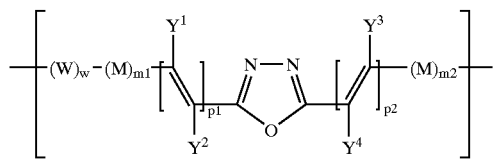

wherein
- W is a straight chain or branched alkylene group with 1 to 22 C-atoms, which is unsubstituted or is mono- or polysubstituted by F, Cl, Br, I or C wherein one or more CH$_2$ groups may optionally be replaced, in each case in independently from one another, by —O—, —S—, —NH—, —NR$^0$—, —CO—, —COO—, —OCO—, —OCO—O—, —S—CO—, —CO—S—, —CH=CH—, —CF=CF— or —C≡C— in such a manner that N, O and/or S atoms are not linked directly to one another;
- R$^0$ is in each case independently H or alkyl with 1 to 12 C-atoms;
- M is, if occuring twice or more, independently of each other, a mesogenic or mesogenity supporting group;
- Y$^1$ to Y$^4$ are in each case independently of each other H, F, Cl or CN;
- w is 1;
- m1, m2 are in each case independently and independently of each other 0 or 1, whereby m1+m2≧1; and
- p1, p2 are in each case independently and independently of each other 0 or 1, whereby p1+p2≧1.

66. An oxadiazole compound according to formula II or formula III another, by —O—, —S—, —NH—, —NR$^0$—, —SiR$^0$R$^{00}$—, —CO—, —COO—, —OCO—, —OCO—O—, —S—CO—, —CO—S—, —CH=CH—, or —C≡C— in such a manner that N, O and/or S are not linked directly to one another;
- P is a polymerizable group;
- Sp is a spacer group or a single bond;
- X is —O—, —S—, —OCH$_2$—, —CH$_2$O—, —CO—, —COO—, —OCO—, —OCO—O—, —CO—NR$^0$—, —NR$^0$—CO—, —OCH$_2$—, —CH$_2$O—, —SCH$_2$—, —CH$_2$S—, —CH=CH—COO—, —OOC—CH=CH—, or a single bond;
- R$^0$, R$^{00}$ are independently of each other H or alkyl with 1 to 12 C-atoms;
- A$^1$, A$^2$ are independently of each other an aromatic group, a heteroarylene group, or a saturated or partially saturated alicyclic or heterocyclic group, in each case having up to 25 C-atoms, and in each case being unsubstituted, mono- or polysubstituted with L;
- L is, if occuring twice or more, independently of each other, F, Cl, CN alkyl with 1 to 6 C-atoms which may is optionally mono- or polysubstituted by F, or alkoxy with 1 to 6 C-atoms which is optionally mono- or polysubstituted by F;
- Z is in each case independently —O—, —S—, —CO—, —COO—, —OCO—, —OCO—O—, —CO—NR$^0$, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$, —CL=CL—, —C≡C—, —CH=CH—COO—, —OCO—CH=CH— or a single bond;
- q$^1$, q$^2$ are independently of each other 0, 1 or 2, whereby q$^1$+q$^2$≧1;

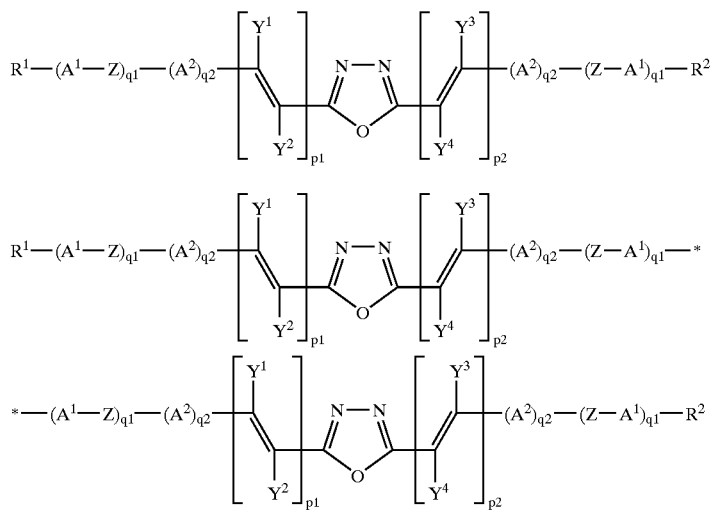

wherein
- R$^1$, R$^2$ are independently of each other H, halogen, —NO$_2$, —CN, —NCS, optionally substituted aryl, optionally substituted heteroarly, optionally substituted arylamino, P—Sp—X, or a straight chain, branched or cyclic alkyl with 1 to 20 C-atoms, which is unsubstituted or is mono- or polysubstituted by F, Cl, Br, I or CN, wherein one or more CH$_2$ groups may optionally be replaced, in each case independently from one
- Y$^1$ to Y$^4$ are in each case independently of each other H, F, Cl or CN;
- p$^1$, p$^2$ are in each case independently and independently of each other 0 or 1 whereby p$^1$+p$^2$≧1; and
- W is a straight chain or branched alkylene group with 1 to 22 C-atoms, which is unsubstituted or is mono- or polysubstituted by F, Cl, Br, I or CN, wherein one or more CH$_2$ groups may optionally be replaced, in each case independently from one another, by —O—, —S—, —NH—, —NR⁰—, —CO—, —COO—, —OCO—, —OCO—O—, —S—CO—, —CO—S—, —CH=CH—, —CF=CF—, or —C≡C— in such a manner that N, O and/or S are not linked directly to one another;

wherein at least one of $R^1$ and $R^2$ is a polymerizable group P—Sp—X—.

67. An oxadiazole compound according to claim 66, wherein $R^1$, $R^2$ are independently of each other H; halogen; —NO₂; —CN; —NCS;

aryl optionally substituted with one or more of halogen, —NO₂,—CN, —NCS, straight chain, branched or cyclic alkyl with 1–20 C atoms, which is unsubstituted mono-, or polysubstituted by F, Cl, Br, I, or CN and in which one or more adjacent CH₂ groups can be replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that N,O and/or S atoms are not linked directly to one another;

heteroaryl optionally substituted with one or more of halogen, —NO₂,—CN, —NCS, straight chain, branched or cyclic alkyl with 1–20 C atoms, which is unsubstituted mono-, or polysubstituted by F, Cl, Br, I, or CN and in which one or more adjacent CH₂ groups can be replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that N,O and/or S atoms are not linked directly to one another;

arylamino wherein the aryl group is optionally substituted with one or more of halogen, —NO₂,—CN, —NCS, straight chain, branched or cyclic alkyl with 1–20 C atoms, which is unsubstituted mono-, or polysubstituted by F, Cl, Br, I, or CN and in which one or more adjacent CH₂ groups can be replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that N,O and/or S atoms are not linked directly to one another, P—Sp—X, or a straight chain, branched or cyclic alkyl with 1 to 20 C-atoms, which is unsubstituted or is mono- or polysubstituted by F, Cl, Br, I or CN, wherein one or more CH₂ groups may optionally be replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CH=CH— or —C≡C— in such a manner that N, O and/or S atoms are not linked directly to one another.

* * * * *

UNITED STATES PATENT AND TRADEMARK OFFICE
CERTIFICATE OF CORRECTION

PATENT NO. : 6,863,841 B2
DATED : March 8, 2005
INVENTOR(S) : Alexander Hahn

It is certified that error appears in the above-identified patent and that said Letters Patent is hereby corrected as shown below:

Column 33,
Line 20, after "$Y^3$" insert -- and --.

Column 37,
Line 18, delete "matter", insert -- manner --.

Column 40,
Line 25, after "to", insert -- s --.

Column 50,
Line 50, delete "C", should read -- CN --.

Column 51,
Line 40, delete "C", should read -- CN --.

Column 52,
Line 29, delete "C", should read -- CN --.

Column 53,
Line 14, delete "C", should read -- CN --.
Formula III, change, "-$(Z-A^1)_{q1}$-" to -- -$(Z-A^1)_{q1}$-W- --.

Signed and Sealed this

Twentieth Day of September, 2005

JON W. DUDAS
*Director of the United States Patent and Trademark Office*